(12) United States Patent
Cowan et al.

(10) Patent No.: US 12,070,568 B2
(45) Date of Patent: Aug. 27, 2024

(54) FLUID MIXING DEVICE AND FLUID DELIVERY TUBE SET INCLUDING SAME

(71) Applicant: BAYER HEALTHCARE LLC, Whippany, NJ (US)

(72) Inventors: Kevin Cowan, Allison Park, PA (US); James Dedig, Pittsburgh, PA (US); Michael Spohn, Fenelton, PA (US); John Haury, Sewickley, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

(21) Appl. No.: 18/324,674

(22) Filed: May 26, 2023

(65) Prior Publication Data
US 2023/0293874 A1 Sep. 21, 2023

Related U.S. Application Data

(63) Continuation of application No. 17/904,399, filed as application No. PCT/US2021/019507 on Feb. 25, 2021, now Pat. No. 11,712,552.
(Continued)

(51) Int. Cl.
| | |
|---|---|
| *A61M 39/10* | (2006.01) |
| *A61M 39/24* | (2006.01) |
| A61M 39/00 | (2006.01) |

(52) U.S. Cl.
CPC .......... *A61M 39/105* (2013.01); *A61M 39/24* (2013.01); *A61M 2039/0027* (2013.01); *A61M 2039/242* (2013.01)

(58) Field of Classification Search
CPC ........ A61M 2039/0027; A61M 39/223; A61M 39/225
See application file for complete search history.

(56) References Cited

U.S. PATENT DOCUMENTS

| | | | |
|---|---|---|---|
| 352,715 | A | 11/1886 | Sandmark |
| 508,584 | A | 11/1893 | Stevens |
| (Continued) | | | |

FOREIGN PATENT DOCUMENTS

| | | |
|---|---|---|
| CN | 103917269 A | 7/2014 |
| CN | 105521533 A | 4/2016 |
| (Continued) | | |

OTHER PUBLICATIONS

International Preliminary Report on Patentability and Written Opinion mailed on Sep. 2, 24015from corresponding PCT Application No. PCT/US2014/026324.
(Continued)

*Primary Examiner* — Courtney B Fredrickson
(74) *Attorney, Agent, or Firm* — Joseph L. Kent; James R. Stevenson; David Schramm

(57) ABSTRACT

A fluid mixing device for mixing a first injection fluid and a second injection fluid includes a first fluid inlet, a second fluid inlet, a mixing chamber in fluid communication with the first and second fluid inlets, and an outlet port in fluid communication with the mixing chamber. The first fluid inlet is configured to conduct the first injection fluid in a first direction and has a first redirecting surface. The second fluid inlet is configured to conduct the second injection fluid in a second direction along a different axis from the first direction and has a second redirecting surface. The mixing chamber is configured to mix the first injection fluid and the second fluid together. The mixture of the first injection fluid and the second injection fluid exits the fluid mixing device via the outlet port.

20 Claims, 19 Drawing Sheets

Related U.S. Application Data

(60) Provisional application No. 62/982,995, filed on Feb. 28, 2020.

(56) References Cited

U.S. PATENT DOCUMENTS

| | | |
|---|---|---|
| 798,093 A | 8/1905 | Edward |
| 817,054 A | 4/1906 | Daniel |
| 937,029 A | 10/1909 | Blessing et al. |
| 945,143 A | 1/1910 | Jacques |
| 1,388,946 A | 8/1921 | Goold |
| 1,930,929 A | 10/1933 | Joel et al. |
| 2,062,285 A | 12/1936 | Sam et al. |
| 2,511,291 A | 6/1950 | Mueller |
| 2,514,575 A | 7/1950 | Hein et al. |
| 2,583,206 A | 1/1952 | Borck et al. |
| 2,592,381 A | 4/1952 | Blackman |
| 2,616,422 A | 11/1952 | Jones |
| 2,667,163 A | 1/1954 | Smith |
| 2,667,164 A | 1/1954 | Smith |
| 2,667,165 A | 1/1954 | Smith |
| 2,667,872 A | 2/1954 | Smith |
| 2,672,866 A | 3/1954 | Kater |
| 2,673,561 A | 3/1954 | Peterson, Jr. |
| 2,688,963 A | 9/1954 | Smith |
| 2,688,964 A | 9/1954 | Smith |
| 2,690,179 A | 9/1954 | Fox |
| 2,717,598 A | 9/1955 | Krasno |
| 2,805,662 A | 9/1957 | Lawshe et al. |
| 2,911,972 A | 11/1959 | Elinger |
| 2,915,986 A | 12/1959 | Sisson |
| 2,935,067 A | 5/1960 | Bouet |
| 2,950,717 A | 8/1960 | Bonet |
| 3,101,712 A | 8/1963 | Strazdins et al. |
| 3,155,281 A | 11/1964 | Stracey |
| 3,159,312 A | 12/1964 | Van, II |
| 3,161,194 A | 12/1964 | Chapman |
| 3,161,195 A | 12/1964 | Taylor et al. |
| 3,166,070 A | 1/1965 | Everett |
| 3,172,577 A | 3/1965 | Hartung |
| 3,190,619 A | 6/1965 | Penney et al. |
| 3,199,511 A | 8/1965 | Kulick |
| 3,231,139 A | 1/1966 | Bouet |
| 3,276,472 A | 10/1966 | Jinkens et al. |
| 3,301,293 A | 1/1967 | Santelli |
| 3,340,869 A | 9/1967 | Bane |
| 3,353,537 A | 11/1967 | Knox et al. |
| 3,390,821 A | 7/1968 | Mullan |
| 3,411,503 A | 11/1968 | Santomieri |
| 3,412,906 A | 11/1968 | Dinger |
| 3,442,424 A | 5/1969 | Sam et al. |
| 3,471,058 A | 10/1969 | Peter et al. |
| 3,473,524 A | 10/1969 | John |
| 3,474,844 A | 10/1969 | Rudolph et al. |
| 3,506,163 A | 4/1970 | James et al. |
| 3,507,278 A | 4/1970 | Winfried |
| 3,527,215 A | 9/1970 | Harry |
| 3,557,788 A | 1/1971 | Betty |
| 3,613,963 A | 10/1971 | Otto |
| 3,618,846 A | 11/1971 | Patrick |
| 3,635,444 A | 1/1972 | Potter |
| 3,671,208 A | 6/1972 | Wayne |
| 3,699,961 A | 10/1972 | Szpur |
| 3,719,207 A | 3/1973 | Takeda |
| 3,736,932 A | 6/1973 | Satchell |
| 3,785,367 A | 1/1974 | Fortin et al. |
| 3,826,409 A | 7/1974 | Chilcoate |
| 3,868,967 A * | 3/1975 | Harding .................. F16K 19/00 366/181.5 |
| 3,873,003 A | 3/1975 | Seiferth et al. |
| 3,938,514 A | 2/1976 | Boucher |
| 3,998,223 A | 12/1976 | Dawe |
| 4,035,461 A | 7/1977 | Korth |
| 4,041,944 A | 8/1977 | Rhodes |
| 4,044,836 A | 8/1977 | Martin et al. |
| 4,064,879 A | 12/1977 | Leibinsohn |
| 4,066,080 A | 1/1978 | Sneider |
| 4,131,217 A | 12/1978 | Sandegren |
| 4,136,802 A | 1/1979 | Mascia et al. |
| 4,140,117 A | 2/1979 | Buckles et al. |
| 4,171,698 A | 10/1979 | Genese |
| 4,204,775 A | 5/1980 | Speer |
| 4,208,136 A | 6/1980 | King et al. |
| 4,236,516 A | 12/1980 | Nilson |
| 4,245,655 A | 1/1981 | Patel |
| 4,312,344 A | 1/1982 | Nilson |
| 4,318,400 A | 3/1982 | Peery et al. |
| 4,325,369 A | 4/1982 | Nilson |
| 4,329,067 A | 5/1982 | Goudy, Jr. |
| 4,349,129 A | 9/1982 | Amneus |
| 4,392,491 A | 7/1983 | Takasugi et al. |
| 4,411,656 A | 10/1983 | Cornett, III |
| 4,419,096 A | 12/1983 | Leeper et al. |
| 4,438,845 A | 3/1984 | Mochow |
| 4,441,823 A | 4/1984 | Power et al. |
| 4,444,310 A | 4/1984 | Odell |
| 4,526,296 A | 7/1985 | Berger et al. |
| 4,610,665 A | 9/1986 | Matsumoto et al. |
| 4,741,733 A | 5/1988 | Winchell et al. |
| 4,747,839 A | 5/1988 | Tarello et al. |
| 4,753,638 A | 6/1988 | Peters |
| 4,773,458 A | 9/1988 | Touzani |
| 4,824,145 A | 4/1989 | Carlsson |
| 4,850,807 A | 7/1989 | Frantz |
| 4,895,570 A | 1/1990 | Larkin |
| 4,904,239 A | 2/1990 | Winchell et al. |
| 4,952,068 A | 8/1990 | Flint |
| 4,969,879 A | 11/1990 | Lichte |
| 5,000,739 A | 3/1991 | Kulisz et al. |
| 5,011,477 A | 4/1991 | Winchell et al. |
| 5,026,348 A | 6/1991 | Venegas |
| 5,033,631 A | 7/1991 | Nightingale |
| 5,048,684 A | 9/1991 | Scott |
| 5,120,315 A | 6/1992 | Hessel |
| 5,147,311 A | 9/1992 | Pickhard |
| 5,163,928 A | 11/1992 | Hobbs et al. |
| 5,178,610 A | 1/1993 | Tsujikawa et al. |
| 5,192,272 A | 3/1993 | Faure |
| 5,199,567 A | 4/1993 | Discko, Jr. |
| 5,201,438 A | 4/1993 | Norwood |
| 5,209,372 A | 5/1993 | Norwood |
| 5,236,204 A | 8/1993 | Hempel |
| 5,237,309 A | 8/1993 | Frantz et al. |
| 5,238,003 A | 8/1993 | Baidwan et al. |
| 5,238,150 A | 8/1993 | Williams |
| 5,240,130 A | 8/1993 | Osbakk |
| 5,242,422 A | 9/1993 | Schneberger et al. |
| 5,263,940 A | 11/1993 | Kriesel |
| 5,269,428 A | 12/1993 | Gilbert |
| 5,312,018 A | 5/1994 | Evezich |
| 5,316,452 A | 5/1994 | Bogen et al. |
| 5,318,520 A | 6/1994 | Nakao |
| 5,318,540 A | 6/1994 | Athayde et al. |
| 5,333,761 A | 8/1994 | Davis et al. |
| 5,342,313 A | 8/1994 | Campbell et al. |
| 5,353,961 A | 10/1994 | Debush |
| 5,370,250 A | 12/1994 | Gilbert |
| 5,383,858 A | 1/1995 | Reilly et al. |
| 5,397,157 A | 3/1995 | Hempel et al. |
| 5,399,173 A | 3/1995 | Parks et al. |
| 5,431,185 A | 7/1995 | Shannon et al. |
| 5,492,147 A | 2/1996 | Challender et al. |
| 5,507,535 A | 4/1996 | McKamey et al. |
| 5,520,653 A | 5/1996 | Reilly et al. |
| 5,573,129 A | 11/1996 | Nagata et al. |
| 5,578,005 A | 11/1996 | Sancoff et al. |
| 5,584,413 A | 12/1996 | Jung |
| 5,592,948 A | 1/1997 | Gatten |
| 5,609,580 A | 3/1997 | Kwiatkowski et al. |
| 5,615,791 A | 4/1997 | Vatelot et al. |
| 5,638,995 A | 6/1997 | Mazda |
| 5,651,776 A | 7/1997 | Appling et al. |
| 5,683,369 A | 11/1997 | Tsukada |
| 5,725,500 A | 3/1998 | Micheler |

(56) References Cited

U.S. PATENT DOCUMENTS

| | | |
|---|---|---|
| 5,758,789 A | 6/1998 | Shin et al. |
| 5,794,107 A | 8/1998 | Russell |
| 5,827,233 A | 10/1998 | Futagawa et al. |
| 5,836,922 A | 11/1998 | Hansen et al. |
| 5,873,861 A | 2/1999 | Hitchins et al. |
| 5,893,843 A | 4/1999 | Rodrigues Claro |
| 5,899,889 A | 5/1999 | Futagawa et al. |
| 5,935,105 A | 8/1999 | Manning et al. |
| 5,957,898 A | 9/1999 | Jepson et al. |
| RE36,377 E | 11/1999 | Gilbert |
| 5,976,112 A | 11/1999 | Lyza, Jr. |
| 5,979,326 A | 11/1999 | Ohinata |
| 5,980,489 A | 11/1999 | Kriesel |
| 5,984,378 A | 11/1999 | Ostrander et al. |
| 6,054,194 A | 4/2000 | Kane |
| 6,056,724 A | 5/2000 | Lacroix |
| 6,062,437 A | 5/2000 | Mascitelli |
| 6,063,058 A | 5/2000 | Sakamoto |
| 6,077,252 A | 6/2000 | Siegel |
| 6,105,815 A | 8/2000 | Mazda |
| 6,132,396 A | 10/2000 | Antanavich et al. |
| 6,142,976 A | 11/2000 | Kubo |
| 6,159,183 A | 12/2000 | Neer et al. |
| 6,177,049 B1 | 1/2001 | Schnell et al. |
| 6,216,915 B1 | 4/2001 | Harman et al. |
| 6,224,577 B1 | 5/2001 | Dedola et al. |
| 6,250,505 B1 | 6/2001 | Petit |
| 6,270,482 B1 | 8/2001 | Rosoff et al. |
| 6,306,191 B1 | 10/2001 | McInerney et al. |
| 6,315,761 B1 | 11/2001 | Shcherbina et al. |
| 6,319,235 B1 | 11/2001 | Yoshino |
| 6,322,535 B1 | 11/2001 | Hitchins et al. |
| 6,322,542 B1 | 11/2001 | Nilson et al. |
| 6,328,715 B1 | 12/2001 | Dragan et al. |
| 6,332,876 B1 | 12/2001 | Poynter et al. |
| 6,442,418 B1 | 8/2002 | Evans, III et al. |
| 6,450,993 B1 | 9/2002 | Lin |
| 6,465,024 B1 | 10/2002 | Di et al. |
| 6,485,471 B1 | 11/2002 | Zivitz et al. |
| 6,497,684 B2 | 12/2002 | Witowski et al. |
| 6,558,358 B2 | 5/2003 | Rosoff et al. |
| 6,575,930 B1 | 6/2003 | Trombley, III et al. |
| 6,578,738 B1 | 6/2003 | Keller |
| 6,616,000 B1 | 9/2003 | Renz |
| 6,620,134 B1 | 9/2003 | Trombley, III et al. |
| 6,634,524 B1 | 10/2003 | Helmenstein |
| 6,643,537 B1 | 11/2003 | Zatezalo et al. |
| 6,652,489 B2 | 11/2003 | Trocki et al. |
| 6,702,143 B2 | 3/2004 | Wang |
| 6,716,195 B2 | 4/2004 | Nolan, Jr. et al. |
| 6,723,074 B1 | 4/2004 | Halseth |
| 6,726,657 B1 | 4/2004 | Dedig et al. |
| 6,731,971 B2 | 5/2004 | Evans et al. |
| 6,773,417 B2 | 8/2004 | Fitzgibbons et al. |
| 6,840,164 B2 | 1/2005 | Eastman |
| 6,855,130 B2 | 2/2005 | Saulenas et al. |
| 6,866,039 B1 | 3/2005 | Wright et al. |
| 6,866,654 B2 | 3/2005 | Callan et al. |
| 6,869,419 B2 | 3/2005 | Dragan et al. |
| 6,921,384 B2 | 7/2005 | Reilly et al. |
| RE38,770 E | 8/2005 | Gilbert |
| 6,974,443 B2 | 12/2005 | Reilly et al. |
| 6,984,222 B1 | 1/2006 | Hitchins et al. |
| 7,004,213 B2 | 2/2006 | Hansen |
| 7,011,650 B2 | 3/2006 | Rosoff et al. |
| 7,094,216 B2 | 8/2006 | Trombley, III et al. |
| 7,101,352 B2 | 9/2006 | Duchon et al. |
| 7,192,416 B1 | 3/2007 | Lazzaro et al. |
| 7,192,549 B2 | 3/2007 | Hansen |
| 7,240,926 B2 | 7/2007 | Dalle et al. |
| 7,250,039 B2 | 7/2007 | Fitzgerald |
| 7,309,463 B2 | 12/2007 | Hansen |
| 7,351,221 B2 | 4/2008 | Trombley, III et al. |
| 7,419,478 B1 | 9/2008 | Reilly et al. |
| 7,427,281 B2 | 9/2008 | Uber et al. |
| 7,457,804 B2 | 11/2008 | Uber, III et al. |
| 7,462,166 B2 | 12/2008 | Kowan et al. |
| 7,497,843 B1 | 3/2009 | Castillo et al. |
| 7,513,378 B2 | 4/2009 | Mori et al. |
| 7,540,856 B2 | 6/2009 | Hitchins et al. |
| 7,556,619 B2 | 7/2009 | Spohn et al. |
| 7,563,249 B2 | 7/2009 | Schriver et al. |
| 7,581,559 B2 | 9/2009 | Bausmith et al. |
| 7,597,683 B2 | 10/2009 | Myhrberg et al. |
| 7,604,623 B2 | 10/2009 | Brunner et al. |
| 7,611,503 B2 | 11/2009 | Spohn et al. |
| 7,621,395 B2 | 11/2009 | Mogensen et al. |
| 7,686,788 B2 | 3/2010 | Freyman et al. |
| 7,766,883 B2 | 8/2010 | Rellly et al. |
| 7,802,691 B2 | 9/2010 | Musalek et al. |
| 7,818,992 B2 | 10/2010 | Riley et al. |
| 7,861,893 B2 | 1/2011 | Voegele et al. |
| 7,996,381 B2 | 8/2011 | Uber, III et al. |
| 8,057,406 B2 | 11/2011 | Mohiuddin |
| 8,147,464 B2 | 4/2012 | Spohn et al. |
| 8,162,903 B2 | 4/2012 | Reilly et al. |
| 8,337,456 B2 | 12/2012 | Schriver et al. |
| 8,388,580 B2 | 3/2013 | Schriver et al. |
| 8,419,676 B2 | 4/2013 | Evans et al. |
| 8,439,863 B2 | 5/2013 | Fago et al. |
| 8,521,716 B2 | 8/2013 | Uber, III et al. |
| 8,740,877 B2 | 6/2014 | Borlaug et al. |
| 8,795,240 B2 | 8/2014 | Chelak |
| 8,872,708 B2 | 10/2014 | Hill et al. |
| 8,882,702 B2 | 11/2014 | Suchecki et al. |
| 8,882,708 B2 | 11/2014 | Hieb et al. |
| 8,919,384 B2 | 12/2014 | Spohn et al. |
| 8,992,489 B2 | 3/2015 | Spohn et al. |
| 9,173,995 B1 | 11/2015 | Tucker et al. |
| 9,180,252 B2 | 11/2015 | Gelblum et al. |
| 9,180,260 B2 | 11/2015 | Huang et al. |
| 9,199,033 B1 | 12/2015 | Cowan et al. |
| 9,474,857 B2 | 10/2016 | Riley et al. |
| 9,498,570 B2 | 11/2016 | Cowan et al. |
| 9,555,379 B2 | 1/2017 | Schriver et al. |
| 9,566,381 B2 | 2/2017 | Barron et al. |
| 9,649,436 B2 | 5/2017 | Capone et al. |
| 9,901,671 B2 | 2/2018 | Toews et al. |
| 10,022,493 B2 | 7/2018 | Shearer, Jr. et al. |
| 10,046,106 B2 | 8/2018 | Cowan et al. |
| 10,105,491 B2 | 10/2018 | Gelblum et al. |
| 10,188,849 B2 | 1/2019 | Fangrow |
| 10,201,666 B2 | 2/2019 | Cowan et al. |
| 10,398,353 B2 | 9/2019 | Addison et al. |
| 10,420,902 B2 | 9/2019 | Cowan et al. |
| 10,507,319 B2 | 12/2019 | Haury et al. |
| 10,549,084 B2 | 2/2020 | Sokolov et al. |
| 10,857,345 B2 | 12/2020 | Uber, III et al. |
| 10,933,190 B2 | 3/2021 | Berry et al. |
| 11,083,882 B2 | 8/2021 | Schrauder et al. |
| 11,207,462 B2 | 12/2021 | Cowan et al. |
| 11,389,585 B2 | 7/2022 | Spohn et al. |
| 11,547,793 B2 | 1/2023 | Cowan et al. |
| 11,738,152 B2 | 8/2023 | Haury et al. |
| 2001/0004466 A1 | 6/2001 | Heinz et al. |
| 2001/0018575 A1 | 8/2001 | Lyza |
| 2002/0010596 A1 | 1/2002 | Matory |
| 2002/0147429 A1 | 10/2002 | Cowan et al. |
| 2003/0216695 A1 | 11/2003 | Yang |
| 2003/0226539 A1 | 12/2003 | Kim et al. |
| 2004/0064041 A1 | 4/2004 | Lazzaro et al. |
| 2004/0068224 A1 | 4/2004 | Couvillon et al. |
| 2004/0092905 A1 | 5/2004 | Azzolini |
| 2004/0116893 A1 | 6/2004 | Spohn et al. |
| 2004/0154788 A1 | 8/2004 | Symonds |
| 2004/0186457 A1 | 9/2004 | Truitt et al. |
| 2004/0249344 A1 | 12/2004 | Nemoto et al. |
| 2004/0254541 A1 | 12/2004 | Wong et al. |
| 2005/0082828 A1 | 4/2005 | Wicks et al. |
| 2005/0113754 A1 | 5/2005 | Cowan |
| 2005/0121103 A1 | 6/2005 | Steigerwalt et al. |
| 2006/0052794 A1 | 3/2006 | McGill et al. |
| 2006/0149213 A1 | 7/2006 | Raybuck |
| 2007/0068964 A1 | 3/2007 | Tanaami et al. |

(56) References Cited

U.S. PATENT DOCUMENTS

| | | |
|---|---|---|
| 2007/0129705 A1 | 6/2007 | Trombley et al. |
| 2008/0045925 A1 | 2/2008 | Stepovich et al. |
| 2008/0086087 A1 | 4/2008 | Spohn et al. |
| 2008/0146996 A1 | 6/2008 | Smisson et al. |
| 2009/0069792 A1 | 3/2009 | Frey et al. |
| 2009/0112087 A1 | 4/2009 | Fago |
| 2009/0216192 A1 | 8/2009 | Schriver et al. |
| 2009/0218243 A1 | 9/2009 | Gyrn et al. |
| 2010/0063445 A1 | 3/2010 | Sternberg et al. |
| 2010/0089475 A1 | 4/2010 | Tracey |
| 2010/0091361 A1 | 4/2010 | Yuuki |
| 2010/0114064 A1 | 5/2010 | Kalafut et al. |
| 2010/0286650 A1 | 11/2010 | Fitzgerald |
| 2011/0009826 A1 | 1/2011 | Lewis |
| 2011/0218434 A1 | 9/2011 | Ziemba et al. |
| 2011/0275988 A1 | 11/2011 | Davis et al. |
| 2011/0282196 A1 | 11/2011 | Martz |
| 2012/0020911 A1 | 1/2012 | Seliktar et al. |
| 2012/0101472 A1 | 4/2012 | Schroeder et al. |
| 2012/0123257 A1 | 5/2012 | Stokes, Jr. et al. |
| 2012/0178629 A1 | 7/2012 | Hudson et al. |
| 2012/0217231 A1 | 8/2012 | Moore et al. |
| 2012/0245560 A1 | 9/2012 | Hochman |
| 2012/0253291 A1 | 10/2012 | Ivosevic et al. |
| 2013/0023048 A1 | 1/2013 | Kim et al. |
| 2013/0030291 A1 | 1/2013 | Lewis |
| 2013/0043273 A1 | 2/2013 | Lee et al. |
| 2013/0053774 A1 | 2/2013 | Kirkpatrick |
| 2013/0067416 A1 | 3/2013 | Barron et al. |
| 2013/0204130 A1 | 8/2013 | McArthur et al. |
| 2013/0310756 A1 | 11/2013 | Whalley et al. |
| 2014/0124087 A1 | 5/2014 | Anderson et al. |
| 2014/0261713 A1 | 9/2014 | Schriver et al. |
| 2014/0276652 A1 | 9/2014 | Gittard |
| 2014/0374353 A1 | 12/2014 | Wright et al. |
| 2015/0260325 A1 | 9/2015 | Quick |
| 2016/0030662 A1 | 2/2016 | Uber, III et al. |
| 2016/0250409 A1 | 9/2016 | Dedig et al. |
| 2017/0035974 A1 | 2/2017 | Berry et al. |
| 2017/0100534 A1 | 4/2017 | Fukikoshi et al. |
| 2017/0165427 A1 | 6/2017 | Uber, III et al. |
| 2017/0232173 A1 | 8/2017 | Perry et al. |
| 2018/0161496 A1 | 6/2018 | Berry et al. |
| 2018/0280630 A1 | 10/2018 | Jiang et al. |
| 2018/0296755 A1 | 10/2018 | Dahlin et al. |
| 2019/0240424 A1 | 8/2019 | Yoshioka et al. |
| 2020/0164141 A1 | 5/2020 | Biermann et al. |
| 2020/0206490 A1 | 7/2020 | Bae |
| 2020/0246541 A1 | 8/2020 | Neftel et al. |
| 2021/0023298 A1 | 1/2021 | Mcdermott et al. |
| 2021/0146064 A1 | 5/2021 | Knutsson |
| 2021/0193289 A1 | 6/2021 | Cowan et al. |
| 2021/0220561 A1 | 7/2021 | Spohn et al. |
| 2021/0316065 A1 | 10/2021 | Berry et al. |
| 2021/0353870 A1 | 11/2021 | Volkar et al. |
| 2023/0146744 A1 | 5/2023 | Cowan et al. |
| 2023/0181816 A1 | 6/2023 | Lee |

FOREIGN PATENT DOCUMENTS

| | | |
|---|---|---|
| EP | 0446898 A2 | 9/1991 |
| EP | 1086661 A2 | 3/2001 |
| EP | 1572266 A2 | 9/2005 |
| EP | 1769849 A1 | 4/2007 |
| EP | 1800704 A1 | 6/2007 |
| EP | 2005934 A2 | 12/2008 |
| EP | 2098258 A1 | 9/2009 |
| EP | 2692375 A1 | 2/2014 |
| EP | 2719420 A1 | 4/2014 |
| EP | 2754459 A1 | 7/2014 |
| EP | 2767299 A1 | 8/2014 |
| EP | 3057648 A1 | 8/2016 |
| EP | 2962770 B1 | 3/2017 |
| EP | 3248635 A1 | 11/2017 |
| FR | 1288915 A | 3/1962 |
| GB | 1173662 A | 12/1969 |
| GB | 2214819 A | 9/1989 |
| GB | 2374143 A | 10/2002 |
| JP | H02-88664 | 7/1990 |
| JP | H0849598 A | 2/1996 |
| JP | H0999034 A | 4/1997 |
| JP | 5485885 B2 | 5/2014 |
| JP | 5511409 B2 | 6/2014 |
| JP | 5882595 B2 | 3/2016 |
| JP | 5897798 B2 | 3/2016 |
| JP | 6552258 B2 | 7/2019 |
| JP | 6839853 B2 | 3/2021 |
| NO | 2010014654 A1 | 2/2010 |
| WO | 9221391 A1 | 12/1992 |
| WO | 9528195 A1 | 10/1995 |
| WO | 9707841 A2 | 3/1997 |
| WO | 0204049 A1 | 1/2002 |
| WO | 02066100 A2 | 8/2002 |
| WO | 2004033023 A1 | 4/2004 |
| WO | 2005035995 A1 | 4/2005 |
| WO | 2007133942 A2 | 11/2007 |
| WO | 2008050218 A2 | 5/2008 |
| WO | 2008153831 A2 | 12/2008 |
| WO | 2009038955 A1 | 3/2009 |
| WO | 2010004206 A2 | 1/2010 |
| WO | 2011011346 A1 | 1/2011 |
| WO | 2011125303 A1 | 10/2011 |
| WO | 2011129175 A1 | 10/2011 |
| WO | 2012061140 A1 | 5/2012 |
| WO | 2012155035 A1 | 11/2012 |
| WO | 2013043868 A1 | 3/2013 |
| WO | 2013043881 A1 | 3/2013 |
| WO | 2013043889 A1 | 3/2013 |
| WO | 2014027009 A1 | 2/2014 |
| WO | 2014055283 A1 | 4/2014 |
| WO | 2014160326 A1 | 10/2014 |
| WO | 2015058088 A1 | 4/2015 |
| WO | 2015066506 A2 | 5/2015 |
| WO | 2015164783 A1 | 10/2015 |
| WO | 2016058946 A1 | 4/2016 |
| WO | 2016069711 A1 | 5/2016 |
| WO | 2016069714 A1 | 5/2016 |
| WO | 2016112163 A1 | 7/2016 |
| WO | 2016157886 A1 | 10/2016 |
| WO | 2016172467 A1 | 10/2016 |
| WO | 2016190904 A1 | 12/2016 |
| WO | 2016191485 A1 | 12/2016 |
| WO | 2017040154 A1 | 3/2017 |
| WO | 2017091635 A1 | 6/2017 |
| WO | 2017091636 A1 | 6/2017 |
| WO | 2017091643 A1 | 6/2017 |
| WO | 2018053074 A1 | 3/2018 |
| WO | 2018057386 A1 | 3/2018 |
| WO | 2018218132 A1 | 11/2018 |
| WO | 2019046259 A1 | 3/2019 |
| WO | 2019046260 A1 | 3/2019 |
| WO | 2019046299 A1 | 3/2019 |
| WO | 2019152978 A1 | 8/2019 |
| WO | 2019204605 A1 | 10/2019 |
| WO | 2019204617 A1 | 10/2019 |
| WO | 2020055785 A1 | 3/2020 |
| WO | 2020055818 A1 | 3/2020 |
| WO | 2021050507 A1 | 3/2021 |
| WO | 2021168076 A1 | 8/2021 |
| WO | 2021173743 A1 | 9/2021 |
| WO | 2021188416 A1 | 9/2021 |
| WO | 2021188460 A1 | 9/2021 |
| WO | 2021222619 A1 | 11/2021 |
| WO | 2021247595 A1 | 12/2021 |
| WO | 2021257667 A1 | 12/2021 |
| WO | 2021257699 A1 | 12/2021 |
| WO | 2022035791 A1 | 2/2022 |

(56) References Cited

FOREIGN PATENT DOCUMENTS

| WO | 2022036058 A1 | 2/2022 |
| WO | 2022265695 A1 | 12/2022 |

OTHER PUBLICATIONS

International Search Report and Written Opinion mailed Jul. 18, 2014 from corresponding PCT Application No. PCT/US2014/026324, which was filed on Mar. 13, 2014.

UN Haluk, A New Device Preventing Air Embolism During the Angiography, Air Trap Device: An In-Vitro Experimental Air Emboli Study, Proceedings of the 2019 Design of Medical Devices Conference, 2019.

* cited by examiner

FLUID MIXING DEVICE AND FLUID DELIVERY TUBE SET INCLUDING SAME

CROSS-REFERENCE TO RELATED APPLICATION

The present application is a continuation application from U.S. application Ser. No. 17/904,399, filed 17 Aug. 2022, which is a U.S. national phase application under 35 U.S.C. § 371 of PCT International Application No. PCT/US2021/019507, filed 25 Feb. 2021, and claims priority to U.S. Provisional Application No. 62/982,995, filed 28 Feb. 2020, the disclosures of which are incorporated herein by reference in their entirety.

BACKGROUND OF THE DISCLOSURE

Field of the Disclosure

The present disclosure is related to fluid mixing devices for use with fluid delivery tubing sets configured for use with powered fluid injectors. The present disclosure is also related to fluid delivery tube sets having said fluid mixing devices.

Description of Related Art

In many medical diagnostic and therapeutic procedures, a medical practitioner, such as a physician or radiologist, injects a patient with one or more fluids using a powered fluid injector system. In recent years, a number of powered fluid injector systems for pressurized injection of fluids have been developed for use in procedures such as angiography (CV), computed tomography (CT), molecular imaging (such as PET imaging), and magnetic resonance imaging (MRI). In these imaging procedures, a first injection fluid, such as a contrast agent, may be used to highlight certain internal organs, portions of the circulatory system, or portions of the body during an imaging process. Meanwhile, a second injection fluid, such as saline or a similar flushing agent, may be used to ensure complete injection of the bolus of the contrast agent and/or adjust the concentration of the contrast agent. In some procedures, it may be desirable to deliver a mixture of the first injection fluid and the second injection fluid.

When delivering a mixture of the first injection fluid and the second injection fluid, it is desirable for the two fluids to be mixed well before injection into the patient. However, because the first and second injection fluids typically have different physical properties, for example specific gravity and/or viscosity, the two fluids may not be thoroughly mixed prior to entering the patient's vascular system, leading to reduced image quality. Accordingly, there is a need in the art for improved fluid delivery systems that promote mixing of two or more injection fluids prior to injection into the patient.

SUMMARY OF THE DISCLOSURE

These needs and others may be met by the non-limiting embodiments described herein, which are directed to an improved fluid mixing devices and fluid delivery tube sets including the same.

In some non-limiting embodiments of the present disclosure, a fluid mixing device for mixing a first injection fluid and a second injection fluid may include a first fluid inlet configured to conduct the first injection fluid in a first direction. The first fluid inlet may have a first redirecting surface. The fluid mixing device further may include a second fluid inlet configured to conduct the second injection fluid in a second direction. The second fluid inlet may have a second redirecting surface. The fluid mixing device further may include a mixing chamber in fluid communication with the first fluid inlet and the second fluid inlet and having a third redirecting surface. The mixing chamber may be configured to mix the first injection fluid and the second injection fluid. The fluid mixing device further may include an outlet port in fluid communication with the mixing chamber and distal to the first fluid inlet and the second fluid inlet. The first redirecting surface may be configured to redirect the first injection fluid in a first different direction from the first direction to enter the mixing chamber along the first different direction, and the second redirecting surface may be configured to redirect the second injection fluid in a second different direction from the second direction to enter the mixing chamber along the second different direction. The first different direction and the second different direction may be selected so that the first injection fluid and the second injection fluid contact the third redirecting surface of the mixing chamber to turbulently mix the first injection fluid and second injection fluid in the mixing chamber. A mixture of the first injection fluid and the second injection fluid may exit the fluid mixing device through the outlet port.

In some non-limiting embodiments of the present disclosure, the fluid mixing device further may include at least one of a first check valve in the first fluid inlet, and a second check valve in the second fluid inlet. The first fluid inlet and the second fluid inlet may have a non-circular cross-sectional shape, and the first check valve and the second check valve may have a circular cross-sectional shape.

In some non-limiting embodiments of the present disclosure, the first fluid inlet and the second fluid inlet may have a first inlet port and a second inlet port, respectively. The first redirecting surface and second redirecting surface may be positioned distally relative to the first inlet port and second inlet port, respectively. The third redirecting surface may be positioned proximally relative to the outlet port, the first redirecting surface, and the second redirecting surface.

In some non-limiting embodiments of the present disclosure, the mixing chamber further may include a first inlet, wherein the first inlet of the mixing chamber is distal to the third redirecting surface. The first redirecting surface may be positioned distal to the first fluid inlet and at least partially faces the first inlet to the mixing chamber. The mixing chamber further may include a second inlet, wherein the second inlet of the mixing chamber is-distal to the third redirecting surface. The second redirecting surface may be positioned distal to the second fluid inlet and at least partially faces the second inlet to the mixing chamber.

In some non-limiting embodiments of the present disclosure, at least one of the first redirecting surface and the second redirecting surface may be substantially concave and have a radius of curvature greater than or equal to 90°. At least one of the first redirecting surface and the second redirecting surface may be substantially concave and have a radius of curvature greater than or equal to 150°. The third redirecting surface may have a substantially concave-shaped surface facing the outlet port. The concave-shaped surface may have a radius of curvature of greater than or equal to 90°. The concave-shaped surface may have a radius of curvature of greater than or equal to 150°.

In some non-limiting embodiments of the present disclosure, the first check valve may have a first end in engagement with a first inlet port on the first fluid inlet and a second end in engagement with a first stop element proximal to the first redirecting surface. The second check valve may have a first end in engagement with a second inlet port on the second fluid inlet and a second end in engagement with a second stop element proximal to the second redirecting surface. The first check valve and the second check valve may be reversibly compressible between the first end and the second end in response to first fluid pressure of the first injection fluid flowing through the first inlet port and a second fluid pressure of the second injection fluid flowing through the second fluid port, respectively. The first stop element and the second stop element may have a pointed proximal end. The first inlet port and the second inlet port may have a tapered end surface.

In some non-limiting embodiments of the present disclosure, the outlet port may have an axis parallel to an axis of the first fluid inlet and an axis of the second fluid inlet. The axis of the outlet port may extend between the axis of the first fluid inlet and the axis of the second fluid inlet. An axis of the first fluid inlet may be parallel to and offset from an axis of the second fluid inlet, and the outlet port may have an axis generally perpendicular to the axis of the first fluid inlet and the axis of the second fluid inlet. An axis of the first fluid inlet may be generally perpendicular to an axis of the second fluid inlet, and the outlet port may have an axis generally parallel and coincidental to one of the axis of the first fluid inlet and the axis of the second fluid inlet. An axis of the first fluid inlet may be at an angle of between 130° and 165° with respect to an axis of the second fluid inlet, and the outlet port may have an axis at an angle less than 70° with respect to one of the axis of the first fluid inlet and the axis of the second fluid inlet.

In some non-limiting embodiments of the present disclosure, each of the first redirecting surface and the second redirecting surface may be concave-shaped and face a direction of fluid flow of the first injection fluid in the first fluid inlet and the second injection fluid in the second fluid inlet, respectively. At least one of the first fluid inlet, the second fluid inlet, and the outlet port may have an at least partially helical-shaped rifling on at least a portion of an inner surface of the at least one of the first fluid inlet, the second fluid inlet, and the outlet port for creating a corresponding fluid vortex for at least one of the first injection fluid, the second injection fluid, and the mixture of the first injection fluid and the second injection fluid.

In some non-limiting embodiments of the present disclosure, the outlet port may have at least one baffle member or mixing member disposed in an inner surface thereof.

In some non-limiting embodiments of the present disclosure, the outlet port further may include a pressure isolation valve integrated therewith.

The pressure isolation valve may have a first lumen in fluid communication with the outlet port, a second lumen configured for connecting to a pressure transducer, and a valve member between the first lumen and the second lumen, wherein the valve member is configured for isolating the second lumen from the outlet port during a fluid injection procedure.

In some non-limiting embodiments of the present disclosure, a connector element may be provided on an exterior or an interior of at least one of the first fluid inlet, the second fluid inlet, and the outlet port.

In some non-limiting embodiments of the present disclosure, a fluid delivery tube set for delivering fluid from a fluid injector to a patient may include: a first inlet tube configured to deliver a first injection fluid; a second inlet tube configured to deliver a second injection fluid; an outlet tube configured to deliver a mixture of the first injection fluid and the second injection fluid to a patient; and a fluid mixing device. The fluid mixing device may include a first fluid inlet configured to conduct the first injection fluid in a first direction. The first fluid inlet may have a first redirecting surface. The fluid mixing device further may include a second fluid inlet configured to conduct the second injection fluid in a second direction. The second fluid inlet may have a second redirecting surface. The fluid mixing device further may include a mixing chamber in fluid communication with the first fluid inlet and the second fluid inlet and having a third redirecting surface. The mixing chamber may be configured to mix the first injection fluid and the second injection fluid. The fluid mixing device further may include an outlet port in fluid communication with the mixing chamber and distal to the first fluid inlet and the second fluid inlet. The first redirecting surface may be configured to redirect the first injection fluid in a first different direction from the first direction to enter the mixing chamber along the first different direction, and the second redirecting surface may be configured to redirect the second injection fluid in a second different direction from the second direction to enter the mixing chamber along the second different direction. The first different direction and the second different direction may be selected so that the first injection fluid and the second injection fluid contact the third redirecting surface of the mixing chamber to turbulently mix the first injection fluid and the second injection fluid in the mixing chamber. A mixture of the first injection fluid and the second injection fluid may exit the fluid mixing device through the outlet port.

In some non-limiting embodiments of the present disclosure, a method for turbulently mixing a first injection fluid and a second injection fluid to form a substantially homogeneous mixture of the first injection fluid and the second injection fluid may include contacting a fluid flow of the first injection fluid with a first concave redirecting surface associated with a first fluid inlet. The method further may include redirecting the fluid flow of the first injection fluid to a first different direction, wherein the first different direction flows at an angle ranging from 90-175° from a fluid flow direction of the first injection fluid and towards a third concave redirecting surface in a mixing chamber. The method further may include contacting a fluid flow of the second injection fluid with a second concave redirecting surface associated with a second fluid inlet. The method further may include redirecting the fluid flow of the second injection fluid to a second different direction, wherein the second different direction flows at an angle ranging from 90-175° from a fluid flow direction of the second injection fluid and towards the third concave redirecting surface in the mixing chamber. The method further may include turbulently mixing the first injection fluid and the second injection fluid in the mixing chamber upon contact of the first injection fluid and the second injection fluid with the third concave redirecting surface to form a mixture of the first injection fluid and the second injection fluid; and redirecting the mixture of the first injection fluid and the second injection fluid through an outlet port of the mixing chamber.

Various other non-limiting embodiments of the present disclosure are recited in one or more of the following clauses:

Clause 1. A fluid mixing device for mixing a first injection fluid and a second injection fluid, the fluid mixing device comprising: a first fluid inlet configured to conduct the first injection fluid in a first direction, the first fluid inlet having a first redirecting surface; a second fluid inlet configured to conduct the second injection fluid in a second direction, the second fluid inlet having a second redirecting surface; a mixing chamber in fluid communication with the first fluid inlet and the second fluid inlet and having a third redirecting surface, the mixing chamber configured to mix the first injection fluid and the second injection fluid; and an outlet port in fluid communication with the mixing chamber and distal to the first fluid inlet and the second fluid inlet, wherein the first redirecting surface is configured to redirect the first injection fluid in a first different direction from the first direction to enter the mixing chamber along the first different direction, and the second redirecting surface is configured to redirect the second injection fluid in a second different direction from the second direction to enter the mixing chamber along the second different direction, wherein the first different direction and the second different direction are selected so that the first injection fluid and the second injection fluid contact the third redirecting surface of the mixing chamber to turbulently mix the first injection fluid and the second injection fluid in the mixing chamber, and wherein a mixture of the first injection fluid and the second injection fluid exits the fluid mixing device through the outlet port.

Clause 2. The fluid mixing device of clause 1, further comprising at least one of a first check valve in the first fluid inlet; and a second check valve in the second fluid inlet.

Clause 3. The fluid mixing device of clause 2, wherein the first fluid inlet and the second fluid inlet have a non-circular cross-sectional shape, and wherein the first check valve and the second check valve have a circular cross-sectional shape.

Clause 4. The fluid mixing device of any one of clauses 1 to 3, wherein the first fluid inlet and the second fluid inlet have a first inlet port and a second inlet port, respectively, wherein the first redirecting surface and second redirecting surface are positioned distally relative to the first inlet port and second inlet port, respectively, and wherein the third redirecting surface is positioned proximally relative to the outlet port, the first redirecting surface, and the second redirecting surface.

Clause 5. The fluid mixing device of any one of clauses 1 to 4, wherein the mixing chamber further comprises a first inlet, wherein the first inlet of the mixing chamber is distal to the third redirecting surface, and wherein the first redirecting surface is positioned distal to the first fluid inlet and at least partially faces the first inlet to the mixing chamber.

Clause 6. The fluid mixing device of any one of clauses 1 to 5, wherein the mixing chamber further comprises a second inlet, wherein the second inlet of the mixing chamber is distant to the third redirecting surface, and wherein the second redirecting surface is positioned distal to the second fluid inlet and at least partially faces the second inlet to the mixing chamber.

Clause 7. The fluid mixing device of any one of clauses 1 to 6, wherein at least one of the first redirecting surface and the second redirecting surface is substantially concave and has a radius of curvature greater than or equal to 90°.

Clause 8. The fluid mixing device of any one of clauses 1 to 6, wherein at least one of the first redirecting surface and the second redirecting surface is substantially concave and has a radius of curvature greater than or equal to 150°.

Clause 9. The fluid mixing device of any of clauses 1 to 8, wherein the third redirecting surface has a substantially concave-shaped surface facing the outlet port.

Clause 10. The fluid mixing device of clause 9, wherein the concave-shaped surface has a radius of curvature of greater than or equal to 90°.

Clause 11. The fluid mixing device of clause 9, wherein the concave-shaped surface has a radius of curvature of greater than or equal to 150°.

Clause 12. The fluid mixing device of any one of clauses 2 to 11, wherein the first check valve has a first end in engagement with a first inlet port on the first fluid inlet and a second end in engagement with a first stop element proximal to the first redirecting surface, wherein the second check valve has a first end in engagement with a second inlet port on the second fluid inlet and a second end in engagement with a second stop element proximal to the second redirecting surface, and wherein the first check valve and the second check valve are reversibly compressible between the first end and the second end in response to first fluid pressure of the first injection fluid flowing through the first inlet port and a second fluid pressure of the second injection fluid flowing through the second fluid port, respectively.

Clause 13. The fluid mixing device of clause 12, wherein the first stop element and the second stop element have a pointed proximal end.

Clause 14. The fluid mixing device of clause any one of clauses 1 to 13, wherein the first inlet port and the second inlet port have a tapered end surface.

Clause 15. The fluid mixing device of any one of clauses 1 to 14, wherein the outlet port has an axis parallel to an axis of the first fluid inlet and an axis of the second fluid inlet.

Clause 16. The fluid mixing device of clause 15, wherein the axis of the outlet port extends between the axis of the first fluid inlet and the axis of the second fluid inlet.

Clause 17. The fluid mixing device of any one of clauses 1 to 14, wherein an axis of the first fluid inlet is parallel to and offset from an axis of the second fluid inlet, and wherein the outlet port has an axis generally perpendicular to the axis of the first fluid inlet and the axis of the second fluid inlet.

Clause 18. The fluid mixing device of any one of clauses 1 to 14, wherein an axis of the first fluid inlet is generally perpendicular to an axis of the second fluid inlet, and wherein the outlet port has an axis generally parallel and coincidental to one of the axis of the first fluid inlet and the axis of the second fluid inlet.

Clause 19. The fluid mixing device of any one of clauses 1 to 14, wherein an axis of the first fluid inlet is at an angle of between 130° and 165° with respect to an axis of the second fluid inlet, and wherein the outlet port has an axis at an angle less than 70° with respect to one of the axis of the first fluid inlet and the axis of the second fluid inlet.

Clause 20. The fluid mixing device of any one of clauses 1 to 19, wherein each of the first redirecting surface and the second redirecting surface are concave-shaped and face a direction of fluid flow of the first injection fluid in the first fluid inlet and the second injection fluid in the second fluid inlet, respectively.

Clause 21. The fluid mixing device of any one of clauses 1 to 20, wherein at least one of the first fluid inlet, the second fluid inlet, and the outlet port has an at least partially helical-shaped rifling on at least a portion of an inner surface of the at least one of the first fluid inlet, the second fluid inlet, and the outlet port for creating a corresponding fluid vortex for at least one of the first injection fluid, the second injection fluid, and the mixture of the first injection fluid and the second injection fluid.

Clause 22. The fluid mixing device of any one of clauses 1 to 21, wherein the outlet port has at least one baffle member or mixing member disposed in an inner surface thereof.

Clause 23. The fluid mixing device of any one of clauses 1 to 22, wherein the outlet port further comprises a pressure isolation valve integrated therewith.

Clause 24. The fluid mixing device of clause 23, wherein the pressure isolation valve comprises a housing having a first lumen in fluid communication with the outlet port, a second lumen configured for connecting to a pressure transducer, and a valve member between the first lumen and the second lumen, wherein the valve member is configured for isolating the second lumen from the outlet port during a fluid injection procedure.

Clause 25. The fluid mixing device of any of clauses 1 to 24, further comprising a connector element on an exterior or an interior of at least one of the first fluid inlet, the second fluid inlet, and the outlet port.

Clause 26. A fluid delivery tube set for delivering fluid from a fluid injector to a patient, the fluid delivery tube set comprising: a first inlet tube configured to deliver a first injection fluid; a second inlet tube configured to deliver a second injection fluid; an outlet tube configured to deliver a mixture of the first injection fluid and the second injection fluid to a patient; and a fluid mixing device comprising: a first fluid inlet coupled to the first inlet tube and configured to conduct the first injection fluid in a first direction, the first fluid inlet having a first redirecting surface; a second fluid inlet coupled to the second inlet tube and configured to conduct the second injection fluid in second direction, the second fluid inlet having a second redirecting surface; a mixing chamber in fluid communication with the first fluid inlet and the second fluid inlet and having a third redirecting surface, the mixing chamber configured to mix the first injection fluid and the second fluid; and an outlet port coupled to the outlet tube and in fluid communication with the mixing chamber, wherein the first redirecting surface is configured to redirect the first injection fluid in a first different direction from the first direction to enter the mixing chamber along the first different direction, and the second redirecting surface is configured to redirect the second injection fluid in a second different direction from the second direction to enter the mixing chamber along the second different direction, wherein the first different direction and the second different direction are selected so that the first injection fluid and the second injection fluid contact the third redirecting surface of the mixing chamber to turbulently mix the first injection fluid and the second injection fluid together in the mixing chamber, and wherein a mixture of the first injection fluid and the second injection fluid exits the fluid mixing device via the outlet port.

Clause 27. The fluid delivery tube set of clause 26, further comprising at least one of a first check valve in the first fluid inlet; and a second check valve in the second fluid inlet.

Clause 28. The fluid delivery tube set of clause 26 or 27, wherein the first fluid inlet and the second fluid inlet have a non-circular cross-sectional shape, and wherein the first check valve and the second check valve have a circular cross-sectional shape.

Clause 29. The fluid delivery tube set of any one of clauses 26 to 28, wherein the first fluid inlet and the second fluid inlet have a first inlet port and a second inlet port, respectively, wherein the first redirecting surface and second redirecting surface are positioned distally relative to the first inlet port and second inlet port, respectively, and wherein the third redirecting surface is positioned proximally relative to the outlet port, the first redirecting surface, and the second redirecting surface.

Clause 30. The fluid delivery tube set of any one of clauses 26 to 29, wherein the mixing chamber further comprises a first inlet, wherein the first inlet of the mixing chamber is distal to the third redirecting surface, and wherein the first redirecting surface is positioned distal to the first fluid inlet and at least partially faces the first inlet to the mixing chamber.

Clause 31. The fluid delivery tube set of any one of clauses 26 to 30, wherein the mixing chamber further comprises a second inlet, wherein the second inlet of the mixing chamber is distal to the third redirecting surface, and wherein the second redirecting surface is positioned distal to the second fluid inlet and at least partially faces the second inlet to the mixing chamber.

Clause 32. The fluid delivery tube set of any one of clauses 26 to 31, wherein at least one of the first redirecting surface and the second redirecting surface is substantially concave and has a radius of curvature greater than or equal to 90°.

Clause 33. The fluid delivery tube set of any one of clauses 26 to 32, wherein at least one of the first redirecting surface and the second redirecting surface is substantially concave and has a radius of curvature greater than or equal to 150°.

Clause 34. The fluid delivery tube set of any of clauses 26 to 33, wherein the third redirecting surface has a substantially concave-shaped surface facing the outlet port.

Clause 35. The fluid delivery tube set of clause 34, wherein the concave-shaped surface has a radius of curvature of greater than or equal to 90°.

Clause 36. The fluid delivery tube set of clause 34, wherein the concave-shaped surface has a radius of curvature of greater than or equal to 150°.

Clause 37. The fluid delivery tube set of any of clauses 26-36, wherein the first check valve has a first end in engagement with a first inlet port on the first fluid inlet and a second end in engagement with a first stop element proximal to the first redirecting surface, wherein the second check valve has a first end in engagement with a second inlet port on the second fluid inlet and a second end in engagement with a second stop element proximal to the second redirecting surface, and wherein the first check valve and the second check valve are reversibly compressible between the first end and the second end in response to a first fluid pressure of the first injection fluid flowing through the first inlet port and a second fluid pressure of the second injection fluid flowing through the second fluid port, respectively.

Clause 38. The fluid delivery tube set of clause 37, wherein the first stop element and the second stop element have a pointed proximal end.

Clause 39. The fluid delivery tube set of any of clauses 26 to 38, wherein the first inlet port and the second inlet port have a tapered end surface.

Clause 40. The fluid delivery tube set of any one of clauses 26 to 39, wherein the outlet port has an axis parallel to an axis of the first fluid inlet and an axis of the second fluid inlet.

Clause 44. The fluid delivery tube set of clause 40, wherein the axis of the outlet port extends between the axis of the first fluid inlet and the axis of the second fluid inlet.

Clause 42. The fluid delivery tube set of any one of clauses 26 to 39, wherein an axis of the first fluid inlet is parallel to and offset from an axis of the second fluid inlet, and wherein the outlet port has an axis generally perpendicular to the axis of the first fluid inlet and the axis of the second fluid inlet.

Clause 43. The fluid delivery tube set of any one of clauses 26 to 39, wherein an axis of the first fluid inlet is generally perpendicular to an axis of the second fluid inlet, and wherein the outlet port has an axis generally parallel and coincidental to one of the axis of the first fluid inlet and the axis of the second fluid inlet.

Clause 44. The fluid delivery tube set of any one of clauses 22 to 39, wherein an axis of the first fluid inlet is at an angle of between 130° and 165° with respect to an axis of the second fluid inlet, and wherein the outlet port has an axis at an angle less than 70° with respect to one of the axis of the first fluid inlet and the axis of the second fluid inlet.

Clause 45. The fluid delivery tube set of any one of clauses 26 to 44, wherein each of the first redirecting surface and the second redirecting surface are concave-shaped and face a direction of fluid flow of the first injection fluid in the first fluid inlet and the second injection fluid in the second fluid inlet, respectively.

Clause 46. The fluid delivery tube set of any one of clauses 26 to 45, wherein at least one of the first fluid inlet, the second fluid inlet, and the outlet port has an at least partially helical-shaped rifling on at least a portion of an inner surface of the at least one of the first fluid inlet, the second fluid inlet, and the outlet port for creating a corresponding fluid vortex for at least one of the first injection fluid, the second injection fluid, and the mixture of the first injection fluid and the second injection fluid.

Clause 47. The fluid delivery tube set of any one of clauses 26 to 46, wherein the outlet port has at least one baffle member or mixing member disposed in an inner surface thereof.

Clause 48. The fluid delivery tube set of any one of clauses 26 to 47, wherein the outlet port further comprises a pressure isolation valve integrated therewith.

Clause 49. The fluid delivery tube set of clause 48, wherein the pressure isolation valve comprises a first lumen in fluid communication with the outlet port, a second lumen configured for connecting to a pressure transducer, and a valve member between the first lumen and the second lumen, wherein the valve member is configured for isolating the second lumen from the outlet port during a fluid injection procedure.

Clause 50. The fluid delivery tube set of any of clauses 26 to 49, further comprising a connector element on an exterior or an interior of at least one of the first fluid inlet, the second fluid inlet, and the outlet port.

Clause 51. A method for turbulently mixing a first injection fluid and a second injection fluid to form a substantially homogeneous mixture of the first injection fluid and the second injection fluid, the method comprising: contacting a fluid flow of the first injection fluid with a first concave redirecting surface associated with a first fluid inlet; redirecting the fluid flow of the first injection fluid to a first different direction, wherein the first different direction flows at an angle ranging from 90-175° from a fluid flow direction of the first injection fluid and towards a third concave redirecting surface in a mixing chamber; contacting a fluid flow of the second injection fluid with a second concave redirecting surface associated with a second fluid inlet; redirecting the fluid flow of the second injection fluid to a second different direction, wherein the second different direction flows at an angle ranging from 90-175° from a fluid flow direction of the second injection fluid and towards the third concave redirecting surface in the mixing chamber; turbulently mixing the first injection fluid and the second injection fluid in the mixing chamber upon contact of the first injection fluid and the second injection fluid with the third concave redirecting surface to form a mixture of the first injection fluid and the second injection fluid; and redirecting the mixture of the first injection fluid and the second injection fluid through an outlet port of the mixing chamber.

Clause 52. The method of clause 51, further comprising at least one of a first check valve in the first fluid inlet; and a second check valve in the second fluid inlet.

Clause 53. The method of clause 52, wherein the first fluid inlet and the second fluid inlet have a non-circular cross-sectional shape, and wherein the first check valve and the second check valve have a circular cross-sectional shape.

Clause 54. The method of any one of clauses 51 to 53, wherein the first fluid inlet and the second fluid inlet have a first inlet port and a second inlet port, respectively, wherein the first redirecting surface and second redirecting surface are positioned distally relative to the first inlet port and second inlet port, respectively, and wherein the third redirecting surface is positioned proximally relative to the outlet port, the first redirecting surface, and the second redirecting surface.

Clause 55. The method of any one of clauses 51 to 54, wherein the mixing chamber further comprises a first inlet, wherein the first inlet of the mixing chamber is distal to the third redirecting surface, and wherein the first redirecting surface is positioned distal to the first fluid inlet and at least partially faces the first inlet to the mixing chamber.

Clause 56. The method of any one of clauses 51 to 55, wherein the mixing chamber further comprises a second inlet, wherein the second inlet of the mixing chamber is distal to the third redirecting surface, and wherein the second redirecting surface is positioned distal to the second fluid inlet and at least partially faces the second inlet to the mixing chamber.

Clause 57. The method of any one of clauses 51 to 56, wherein at least one of the first redirecting surface and the second redirecting surface is substantially concave and has a radius of curvature greater than or equal to 90°.

Clause 58. The method of any one of clauses 51 to 57, wherein at least one of the first redirecting surface and the second redirecting surface is substantially concave and has a radius of curvature greater than or equal to 150°.

Clause 59. The method of any of clauses 51 to 58, wherein the third redirecting surface has a substantially concave-shaped surface facing the outlet port.

Clause 60. The method of clause 59, wherein the concave-shaped surface has a radius of curvature of greater than or equal to 90°.

Clause 61. The method of clause 59, wherein the concave-shaped surface has a radius of curvature of greater than or equal to 150°.

Clause 62. The method of any of clauses 51 to 61, wherein the first check valve has a first end in engagement with a first inlet port on the first fluid inlet and a second end in engagement with a first stop element proximal to the first redirecting surface, wherein the second check valve has a first end in engagement with a second inlet port on the second fluid inlet and a second end in engagement with a second stop element proximal to the second redirecting surface, and wherein the first check valve and the second check valve are reversibly compressible between the first end and the second end in response to a first fluid pressure of the first injection fluid flowing through the first inlet port and a second fluid pressure of the second injection fluid flowing through the second fluid port, respectively.

Clause 63. The method of clause 62, wherein the first stop element and the second stop element have a pointed proximal end.

Clause 64. The method of any of clauses 51 to 63, wherein the first inlet port and the second inlet port have a tapered end surface.

Clause 65. The method of any one of clauses 51 to 64, wherein the outlet port has an axis parallel to an axis of the first fluid inlet and an axis of the second fluid inlet.

Clause 66. The method of clause 65, wherein the axis of the outlet port extends between the axis of the first fluid inlet and the axis of the second fluid inlet.

Clause 67. The method of any one of clauses 51 to 64, wherein an axis of the first fluid inlet is parallel to and offset from an axis of the second fluid inlet, and wherein the outlet port has an axis generally perpendicular to the axis of the first fluid inlet and the axis of the second fluid inlet.

Clause 68. The method of any one of clauses 51 to 64, wherein an axis of the first fluid inlet is generally perpendicular to an axis of the second fluid inlet, and wherein the outlet port has an axis generally parallel and coincidental to one of the axis of the first fluid inlet and the axis of the second fluid inlet.

Clause 69. The method of any one of clauses 51 to 64, wherein an axis of the first fluid inlet is at an angle of between 130° and 165° with respect to an axis of the second fluid inlet, and wherein the outlet port has an axis at an angle less than 70° with respect to one of the axis of the first fluid inlet and the axis of the second fluid inlet.

Clause 70. The method of any one of clauses 51 to 69, wherein each of the first redirecting surface and the second redirecting surface are concave-shaped and face a direction of fluid flow of the first injection fluid in the first fluid inlet and the second injection fluid in the second fluid inlet, respectively.

Clause 71. The method of any one of clauses 51 to 70, wherein at least one of the first fluid inlet, the second fluid inlet, and the outlet port has an at least partially helical-shaped rifling on at least a portion of an inner surface of the at least one of the first fluid inlet, the second fluid inlet, and the outlet port for creating a corresponding fluid vortex for at least one of the first injection fluid, the second injection fluid, and the mixture of the first injection fluid and the second injection fluid.

Clause 72. The method of any one of clauses 51 to 71, wherein the outlet port has at least one baffle member or mixing member disposed in an inner surface thereof.

Clause 73. The method of any one of clauses 51 to 72, wherein the outlet port further comprises a pressure isolation valve integrated therewith.

Clause 74. The method of clause 73, wherein the pressure isolation valve comprises a first lumen in fluid communication with the outlet port, a second lumen configured for connecting to a pressure transducer, and a valve member between the first lumen and the second lumen, wherein the valve member is configured for isolating the second lumen from the outlet port during a fluid injection procedure.

Clause 75. The method of any of clauses 51 to 74, further comprising a connector element on an exterior or an interior of at least one of the first fluid inlet, the second fluid inlet, and the outlet port.

Further details and advantages of the various embodiments described in detail herein will become clear upon reviewing the following detailed description of the various examples in conjunction with the accompanying drawing figures.

DETAILED DESCRIPTION OF THE DISCLOSURE

Figure 1:
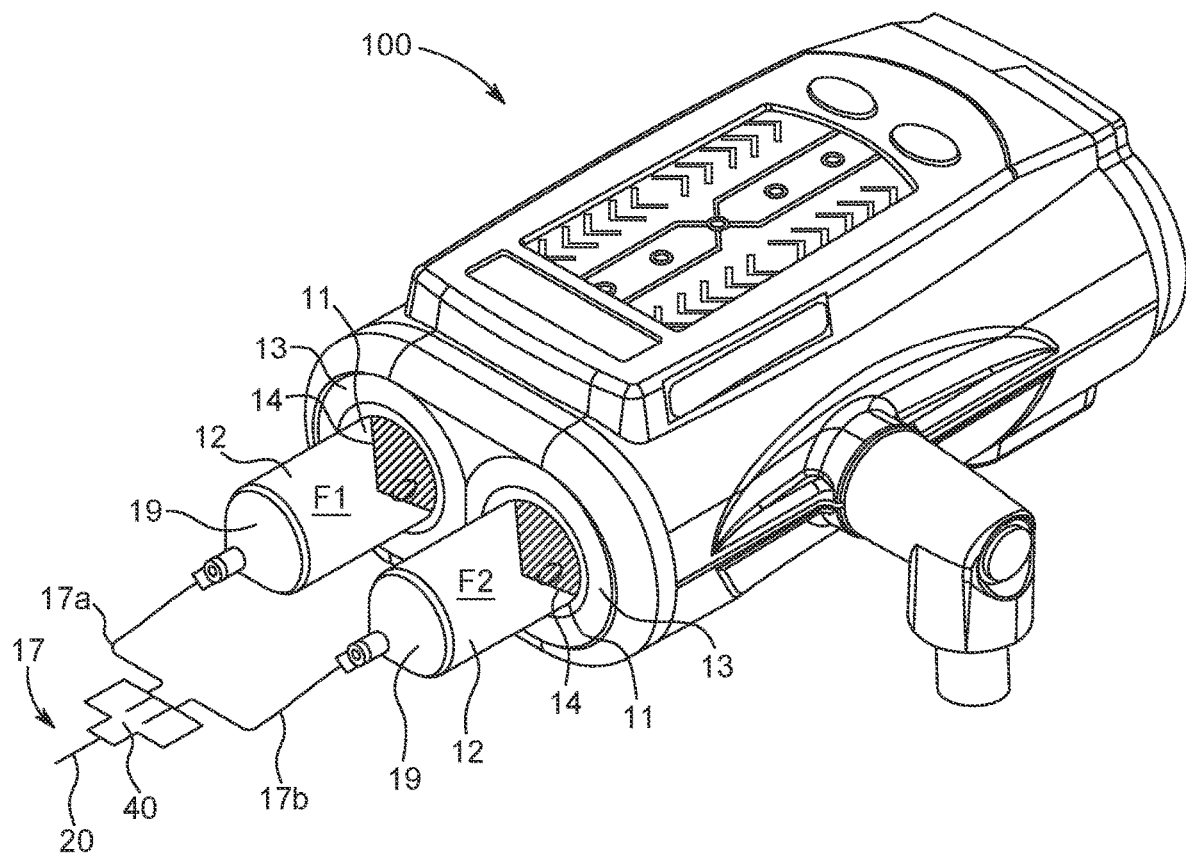
FIG. 1 is a perspective view of a fluid injector system according to some embodiments of the present disclosure.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures.

Spatial or directional terms, such as "left", "right", "inner", "outer", "above", "below", and the like, are not to be considered as limiting as the disclosure can assume various alternative orientations.

All numbers used in the specification and claims are to be understood as being modified in all instances by the term "about". The terms "approximately", "about", and "substantially" mean a range of plus or minus ten percent of the stated value.

Unless otherwise indicated, all ranges or ratios disclosed herein are to be understood to encompass the beginning and ending values and any and all subranges or sub-ratios subsumed therein. For example, a stated range or ratio of "1 to 10" should be considered to include any and all subranges or subratios between (and inclusive of) the minimum value of 1 and the maximum value of 10; that is, all subranges or subratios beginning with a minimum value of 1 or more and ending with a maximum value of 10 or less. The ranges and/or ratios disclosed herein represent the average values over the specified range and/or ratio.

The terms "first", "second", and the like are not intended to refer to any particular order or chronology, but refer to different conditions, properties, or elements.

All documents referred to herein are "incorporated by reference" in their entirety.

The term "at least" is synonymous with "greater than or equal to".

As used herein, the term "at least one of" is synonymous with "one or more of". For example, the phrase "at least one of A, B, and C" means any one of A, B, and C, or any combination of any two or more of A, B, and C. For example, "at least one of A, B, and C" includes one or more of A alone; or one or more B alone; or one or more of C alone; or one or more of A and one or more of B; or one or more of A and one or more of C; or one or more of B and one or more of C; or one or more of all of A, B, and C. Similarly, as used herein, the term "at least two of" is synonymous with "two or more of". For example, the phrase "at least two of D, E, and F" means any combination of any two or more of D, E, and F. For example, "at least two of D, E, and F" includes one or more of D and one or more of E; or one or more of D and one or more of F; or one or more of E and one or more of F; or one or more of all of D, E, and F.

The word "comprising" and "comprises", and the like, does not exclude the presence of elements or steps other than those listed in any claim or the specification as a whole. In the present specification, "comprises" means "includes" and "comprising" means "including".

As used herein, the terms "parallel" or "substantially parallel" mean a relative angle as between two objects (if extended to theoretical intersection), such as elongated objects and including reference lines, that is from 0° to 5°, or from 0° to 3°, or from 0° to 2°, or from 0° to 1°, or from 0° to 0.5°, or from 0° to 0.25°, or from 0° to 0.1°, inclusive of the recited values.

As used herein, the terms "perpendicular", "transverse", "substantially perpendicular", or "substantially transverse" mean a relative angle as between two objects at their real or theoretical intersection is from 85° to 90°, or from 87° to 90°, or from 88° to 90°, or from 89° to 90°, or from 89.5° to 90°, or from 89.75° to 90°, or from 89.9° to 90°, inclusive of the recited values.

It is also to be understood that the specific devices and processes illustrated in the attached drawings, and described in the following specification, are simply exemplary examples of the disclosure. Hence, specific dimensions and other physical characteristics related to the examples disclosed herein are not to be considered as limiting.

When used in relation to a component of a fluid injector system such as a fluid reservoir, a syringe, or a fluid line, the term "distal" refers to a portion of said component nearest to a patient. When used in relation to a component of a fluid injector system such as a fluid reservoir, a syringe, or a fluid line, the term "proximal" refers to a portion of said component nearest to the injector of the fluid injector system (i.e., the portion of said component farthest from the patient). When used in relation to a component of a fluid injector system such as a fluid reservoir, a syringe, or a fluid line, the term "upstream" refers to a direction away from the patient and towards the injector of the fluid injector system. For example, if a first component is referred to as being "upstream" of a second component, the first component is located nearer to the injector along the fluid path than the second component is to the injector. When used in relation to a component of a fluid injector system such as a fluid reservoir, a syringe, or a fluid line, the term "downstream" refers to a direction towards the patient and away from the injector of the fluid injector system. For example, if a first component is referred to as being "downstream" of a second component, the first component is located nearer to the patient along the fluid path than the second component is to the patient.

Although the present disclosure is described primarily in reference to the MEDRAD® Stellant CT Injection System, it will be apparent to persons of ordinary skill in the art that the present disclosure can be applied to a variety of injection systems inclusive of their associated disposables (e.g., syringes, tubing, etc.), such as those designed for CT, CV, MR, PET, ultrasound, and other medical injectors configured to inject two or more medical fluids. In certain embodiments, the fluid mixing device may be suited for use with tubing associated with an angiography injector. Examples of such injection systems include the MEDRAD® Salient CT Injection System, MEDRAD® Stellant FLEX CT Injection System, MEDRAD® Centargo CT Injection System, MEDRAD® MRXperion MR Injection System, MEDRAD® Avanta Injection System, and MEDRAD® Mark 7 Arterion Injection System offered by Bayer HealthCare LLC, Indianola, PA.

Referring now to FIG. 1, a non-limiting example of a fluid injector system 100 in accordance with the present disclosure includes at least one fluid reservoir, such as at least one syringe 12 having a reciprocally-movable plunger 14, at least one piston connectable to the plunger 14, and a fluid control module (not pictured). The fluid injector system 100 may be configured as a computed tomography (CT) contrast injector system, a magnetic resonance imaging (MRI) contrast injector system, or an angiographic (CV) contrast injector system. The at least one syringe 12 is generally adapted to interface with at least one component of the system, such as a syringe port 13. The fluid injector system 100 is generally configured to deliver at least one fluid F from the at least one syringe 12 to a patient during an injection procedure. The fluid injector system 100 is configured to releasably receive the at least one syringe 12, which is to be filled with at least one fluid F, such as a contrast media, saline solution, Ringer's lactate, or any desired medical fluid. The system may be a multi-syringe injector, wherein several syringes may be oriented side-byside or in another spatial relationship and are separately actuated by respective pistons associated with the injector. The at least one syringe 12 may be oriented in any manner such as upright, downright, or positioned at any degree angle.

With continued reference to FIG. 1, the injector system 100 may be a dual syringe fluid injector system used during a medical procedure to inject the at least two injection fluids F1 and F2 into the vasculature system of a patient by driving plungers 14 of respective syringes 12 with a drive member, such as a piston (not shown). Alternatively, one or both of the syringes of the dual head fluid injector system may be replaced with a pump, such as a peristaltic pump, without deviating from the scope of the present disclosure. The first and second injection fluids F1 and F2 may be a suitable contrast imaging agent and a flushing fluid, respectively. The piston may be configured to engage the plunger 14. Upon engagement, the at least one piston may move the plunger 14 toward the distal end 19 of the at least one syringe 12, for example during a fluid delivery operation, as well as retracting the plunger 14 toward the proximal end 11 of the at least one syringe 12, for example during a filling operation to fill the syringe 12.

According to various embodiments, a tubing set 17 (e.g., first and second fluid conduits 17a and 17b configured for connecting to respective first and second syringes 12 and common administration line 20) may be in fluid communication with an outlet port of each syringe 12 to place each syringe in fluid communication with a catheter or other fluid delivery device for delivering the fluid F from each syringe 12 to the a vascular access site. The first and second fluid conduits 17a and 17b may be connected to the common administration line 20 by a fluid mixing device 40 according to various embodiments of the present disclosure. The fluid injector system 100 shown in FIG. 1 is an open system do to the lack of valves configured of isolating the syringes 12 from one another and from at least a portion of the tubing set 17. However, it is to be understood that valves may be added distally of the syringes 12 to convert the fluid injector system 100 of FIG. 1 to a closed system.

For accurate and efficient administration of volumes of contrast agent during an imaging procedure, many injection protocols require a dual flow administration, i.e., where a mixture of both contrast agent and saline are administered concurrently to the patient. However, because the contrast and the flushing fluid (saline) typically have different physical properties, for example specific gravity, viscosity, and/or surface tension properties, the two solutions may not be thoroughly mixed prior to entering the patient's vascular system leading to reduced image quality. For example, in certain cases where inefficient mixing has occurred, laminar flow of the less viscous faster flowing fluid may occur past the more viscous, slower flowing fluid. While Y-connectors and T-connectors for connecting two fluid conduits to a common administration line are known, conventional Y-connectors and T-connectors may not provide sufficient mixing of the two fluids. Turbulent mixing may improve the efficiency of mixing between the viscous contrast agent and less viscous saline. Examples of connectors having turbulent mixing chambers are described in U.S. Pat. No. 9,555,379, the disclosure of which is incorporated herein by reference. The present disclosure describes new fluid mixing devices that provide improved mixing of viscous and less viscous fluids for contrast enhanced imaging procedures.

Figure 2:
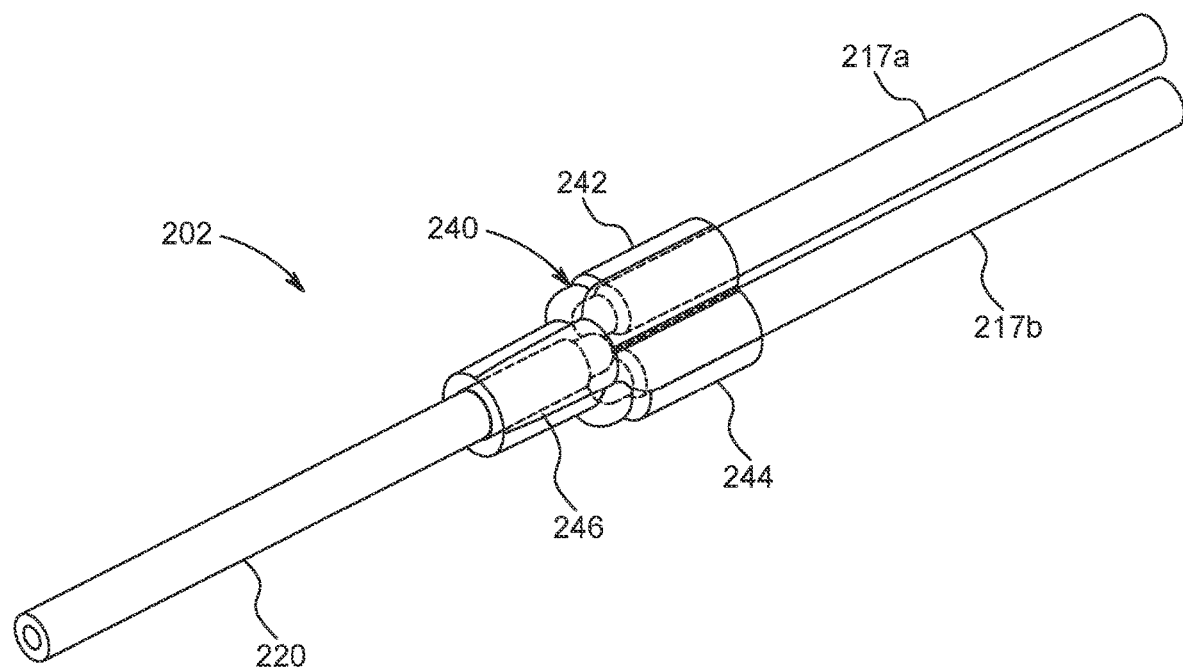
FIG. 2 is a perspective view of a portion of a fluid delivery tube set that may be used with the fluid injector system of FIG. 1.
Figure 3:
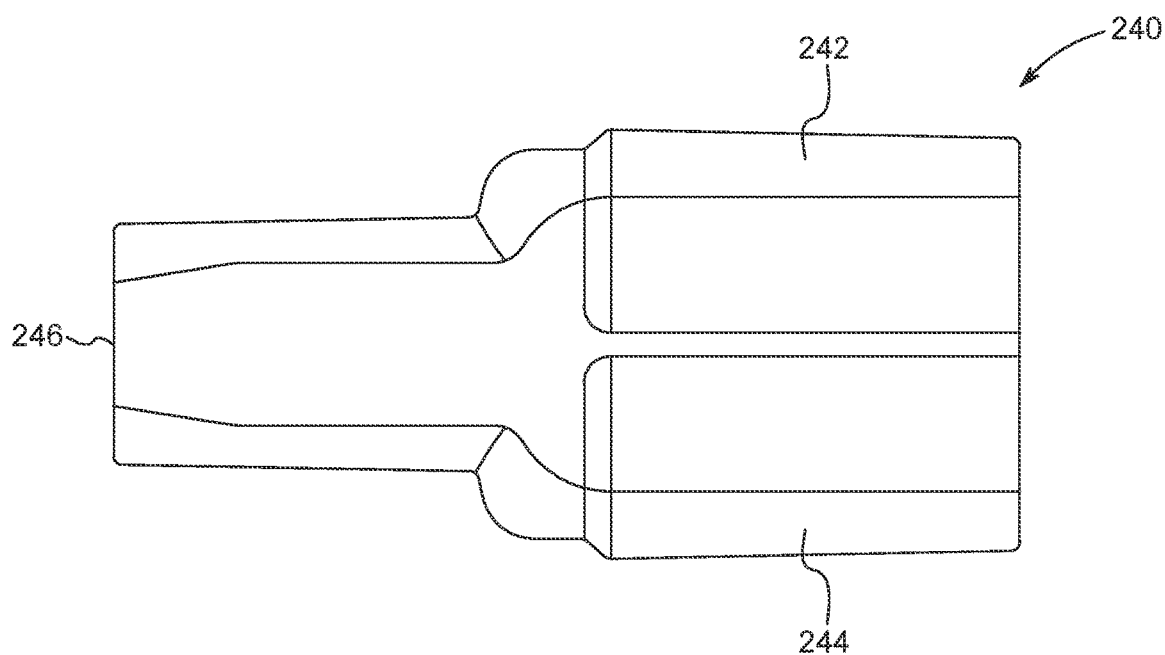
FIG. 3 is a profile view of the fluid mixing device for the fluid delivery tube set of FIG. 2.
Figure 4:
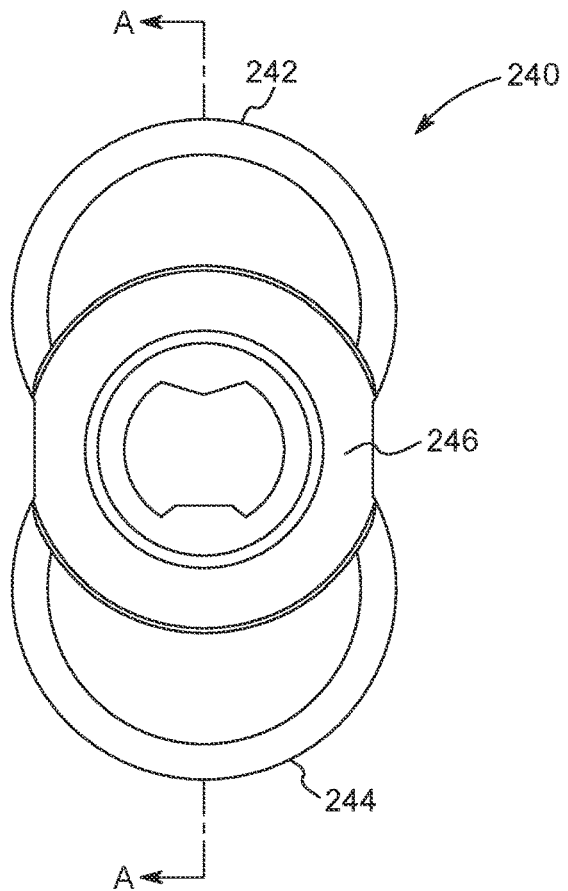
FIG. 4 is a plan view of a distal end of the fluid mixing device of FIG. 3.
Figure 5:
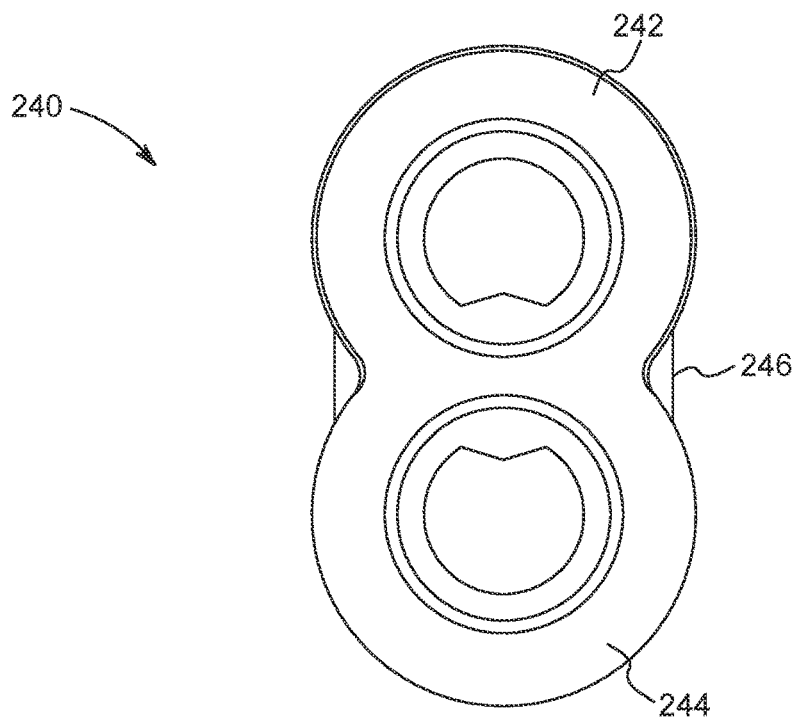
FIG. 5 is a plan view of a proximal end of the fluid mixing device of FIG. 3.

FIG. 2 is a perspective view of a portion of a fluid delivery tube set 202 that may be used with a dual-head injector, such as the fluid injector system 100 of FIG. 1 in place of the tubing set 17, according to some non-limiting embodiments of the present disclosure. As shown, the fluid delivery tube set 202 includes a first inlet line 217a, a second inlet line 217b, an outlet line 220, and a fluid mixing device 240. The first and second inlet lines 217a and 217b are configured to deliver first and second injection fluids, respectively, to the fluid mixing device 240. In one example embodiment, the first and second injection fluids are a contrast media solution and a saline solution, respectively. Furthermore, the outlet line 220 is configured to deliver a mixture of the first and second injection fluids from the fluid mixing device 240 to a patient or other downstream fluid path component (e.g., a prime tube).

Figure 6:
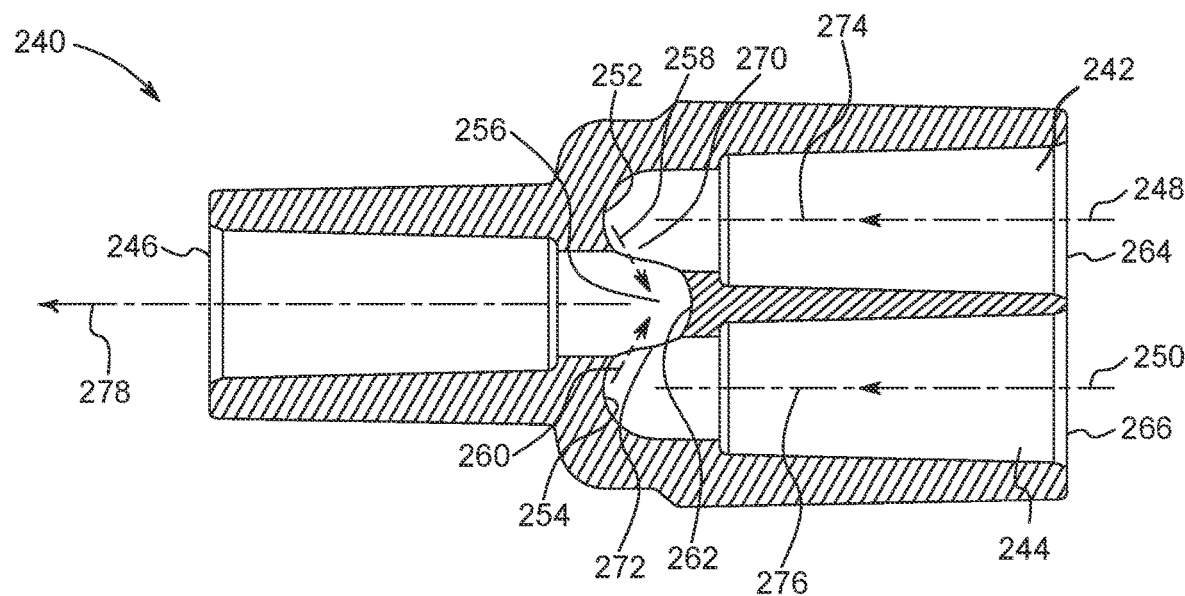
FIG. 6 is a cross-sectional view of the fluid mixing device of FIGS. 3-5, taken along line A-A in FIG. 4.

As will be appreciated herein, the fluid mixing device 240 is configured to mix the first and second injection fluids. FIGS. 3, 4, 5, and 6 show top, left, right, and cross-section views, respectively, of the fluid mixing device 240. As shown in FIG. 6, the fluid mixing device 240 has a body defining first and second fluid inlets 242 and 244, each of which is configured to conduct a corresponding one of the first and second injection fluids in a corresponding first and second direction 248 and 250. As shown, the second direction 250 is along a different axis 276 from the first direction 248. In certain embodiments, the axis of the first direction 248 and the axis of the second direction 250 may be substantially parallel. In other embodiments, the axis of the first direction 248 may be angled at an acute or an obtuse angle relative to the second direction 250.

With continuing reference to FIG. 6, the first and second fluid inlets 242 and 244 have corresponding first and second redirecting surfaces 252 and 254. In certain embodiments, one or both of the first and second redirecting surfaces 252 and 254 are concave-shaped facing the first and second fluid inlets 242 and 244, respectively, to redirect the flow of fluid. Moreover, the fluid mixing device 240 further has a mixing chamber 256 in fluid communication with the first and second fluid inlets 242 and 244 through first and second mixing chamber inlets 270 and 272, and an outlet port 246 in fluid communication with the mixing chamber 256. The mixing chamber 256 is configured to turbulently mix the redirected first and second injection fluids together, for example by turbulently mixing with impact against a third redirecting surface 262 in mixing chamber 256.

More specifically, the first and second redirecting surfaces 252 and 254 are configured to redirect a first fluid and a second fluid entering the first and second fluid inlets 242 and 244, respectively, into the mixing chamber 256 through first and second mixing chamber inlets 270 and 272, where the first and second injection fluids can then be turbulently mixed. Prior to entering the mixing chamber 256, the first and second injection fluids independently flow through the first and second fluid inlets 242, 244, respectively. As the first and second fluids flow through the first and second fluid inlets 242, 244, respectively, the first and second fluids contact the respective first and second redirecting surfaces 252, 254 at distal ends of the first and second fluid inlets 242, 244, respectively. The first and second redirecting surfaces 252 and 254 are configured to redirect the first and second injection fluids in a corresponding first and second different direction 258 and 260 that is different than the corresponding first and second directions 248 and 250. Due to this deflection, the first and second injection fluids enter the mixing chamber 256 through first and second mixing chamber inlets 270 and 272 along the corresponding first and second different directions 258 and 260 where the two fluids come into turbulent contact with one another. The first and second different directions 258 and 260 are selected so that the first and second injection fluids contact a third redirecting surface 262 at a proximal end of the mixing chamber 256 to turbulently mix the first and second injections fluids together in the mixing chamber 256. In some embodiments, the third redirecting surface 262 may have a concave-shaped end facing the outlet port 246.

After mixing, the mixture of the first and second injection fluids exits the fluid mixing device 240 via the outlet port 246 at a distal end of the fluid mixing device 240 in a direction along a third axis 278. In some embodiments, the third axis 278 may be parallel with one or both of the first and second axes 274, 276. In other embodiments, the third axis 278 may be arranged at an acute or obtuse angle relative to both of the first and second axes 274, 276.

With continued reference to FIG. 6, the first and second fluid inlets 242 and 244 each have corresponding first and second inlet ports 264 and 266, configured to respectively attach to a first fluid tubing and a second fluid tubing (shown in FIG. 2). In some embodiments, the first fluid tubing and the second fluid tubing may be removably or non-removably connectable to the first and second inlet ports 264, 266. In embodiments where the first fluid tubing and the second fluid tubing are non-removably connectable to the first and second inlet ports 264, 266, the first fluid tubing and the second fluid tubing may be connected to the first and second inlet ports 264, 266 by solvent bonding, laser welding, or other attachment means.

As shown in FIG. 6, the first and second redirecting surfaces 252 and 254 are positioned distally relative to the first and second inlet ports 264 and 266, respectively, and the third redirecting surface 262 is positioned proximally relative to the outlet port 246, and the first and second redirecting surfaces 252 and 254. In one example embodiment, the first and second redirecting surfaces 252 and 254 are positioned closer to the outlet port 246 compared to the position of the than the third redirecting surface 262 and the outlet port 246. Furthermore, the first and second redirecting surfaces 252 and 254 may be formed at a distal end of the corresponding first and second fluid inlets 242 and 244, and each of the first and second redirecting surfaces 252 and 254 at least partially face the corresponding first and second mixing chamber inlets 270 and 272 to the mixing chamber 256, respectively.

With continued reference to FIG. 6, at least one of the first and second redirecting surfaces 252 and 254 may have a concave surface. Concave surface configuration may improve the redirecting nature of the surface with turbulent flow while eliminating corners in which air bubbles may collect or be temporarily suspended during a priming operation. In some embodiments, each of the first and second redirecting surfaces 252 and 254 may have a radius of curvature greater than or equal to 90°, and in other embodiments being greater than or equal to 150°. For example, in particular embodiments, each of the first and second redirecting surfaces 252 and 254 may have a radius of curvature of from 80° to 160°. In some embodiments, each of the first and second redirecting surfaces 252 and 254 may have a radius of curvature between 90° and 180°. Accordingly, the injection fluid from each of the inlet lines 217a and 217b contacts the radiused redirecting surfaces 252 and 254, which causes the first and second injection fluids to change the flow direction. In some embodiments, the radiused redirecting surfaces 252 and 254 may change the flow direction of the first and second injection fluids, respectively, by an angle ranging from 90° to 150° toward different directions 258 and 260 and into the mixing chamber 256. As such, the fluids double back and interact with each other, e.g., turbulently mix, in the mixing chamber 256 in combination with further redirection by the third redirecting surface 262. After the fluids mix to a homogenous solution, the mixture of fluids is redirected again by the radius of the third redirecting surface 262 along a flow direction of the third axis 278 causing the mixture of the first and second injection fluid to flow down the single outlet line 220. In some embodiments, the third redirecting surface 262 may have a radius of curvature greater than or equal to 90°, more preferably being greater than or equal to 150°. In some embodiments, the third redirecting surface 262 may have a radius of curvature between 90° and 180°. While known mixing devices (not shown) include some swirling of the injection fluids, various conventional mixing devices may still suffer from a density separation, e.g., higher density fluid spinning to the outside of the lower density fluid, which prevents thorough mixing of the first and second fluids. The fluid mixing device 240, by way of contrast, produces a substantially homogeneous mixture of the first and second injection fluids during the turbulent mixing process.

According to various embodiments, the first and second redirecting surfaces 252 and 254 may include concave-shaped redirecting surfaces that face directions of flow in the first fluid inlet 242 and the second fluid inlet 244, respectively. Additionally, as shown in FIG. 6, the first fluid inlet 242, the second fluid inlet 244, and the outlet port 246 all have corresponding axes 274, 276, and 278. In some embodiments, the third axis 278 of the outlet port 246 may be positioned between the first and second axes 274 and 276 of the first and second fluid inlets 242 and 244, respectively. In other embodiments, the third axis 278 of the outlet port 246 may be positioned above or below the first and second axes 274 and 276 of the first and second fluid inlets 242 and 244, respectively. In other embodiments, the third axis 278 of the outlet port 246 may be coaxial with one of the first and second axes 274 and 276 of the first and second fluid inlets 242 and 244. In other embodiments, the first and second different direction 258 and 260 of the fluids entering the mixing chamber 256 may be angled toward each other with a 0 degree to 90 degree angle so that the first and second fluids directly impact each other and turbulently mix.

In operation, the first injection fluid enters the first fluid inlet 242 and the second injection fluid enters the second fluid inlet 244, each from a corresponding one of the first and second inlet lines 217a and 217b (shown in FIG. 2). The first and second injection fluids then pass through the respective first and second fluid inlets 242 and 244 until they reach the first and second redirecting surfaces 252 and 254. When the first injection fluid engages the first redirecting surface 252, the first fluid is redirected in the direction 258 into the mixing chamber 256. Similarly, when the second injection fluid engages the second redirecting surface 254 through first mixing chamber inlet 270, the second fluid is redirected in the direction 260 into the mixing chamber 256. At this point, the first and second injection fluids, by having been redirected into the mixing chamber 256 through the second mixing chamber inlet 272, are turbulently mixed together by the flow of the first and second fluids impacting each other and the third redirecting surface 262 in the mixing chamber 256. The mixture of the first and second injection fluids is simultaneously engaged with the third redirecting surface 262, upon which time it is redirected through the outlet port 246 and into the outlet line 220, in order to be delivered to the patient or other downstream fluid path component. According to various embodiments, the first and second fluids may be at least partially redirected to flow in opposite directions, such as one flowing in a clockwise direction and the other flowing in a counter-clockwise direction in the mixing chamber 256 such that the flow of the first and second fluids engage and impact each other head on to create turbulent mixing. For example, the change of inertia associated with the impact of one fluid flowing in a clockwise flow direction and the other fluid flowing in a counterclockwise flow direction results in a turbulently mixed solution of the first and second fluid as the two fluids interact within mixing chamber 256. Depending on the mixing ratio and flow rates of the first and second injection fluids, the first and second injection fluids may mix solely in the mixing chamber 256, or in the mixing chamber 256 and in the area of at least one of first redirecting surface 252 and second redirecting surface 254.

Figure 7:
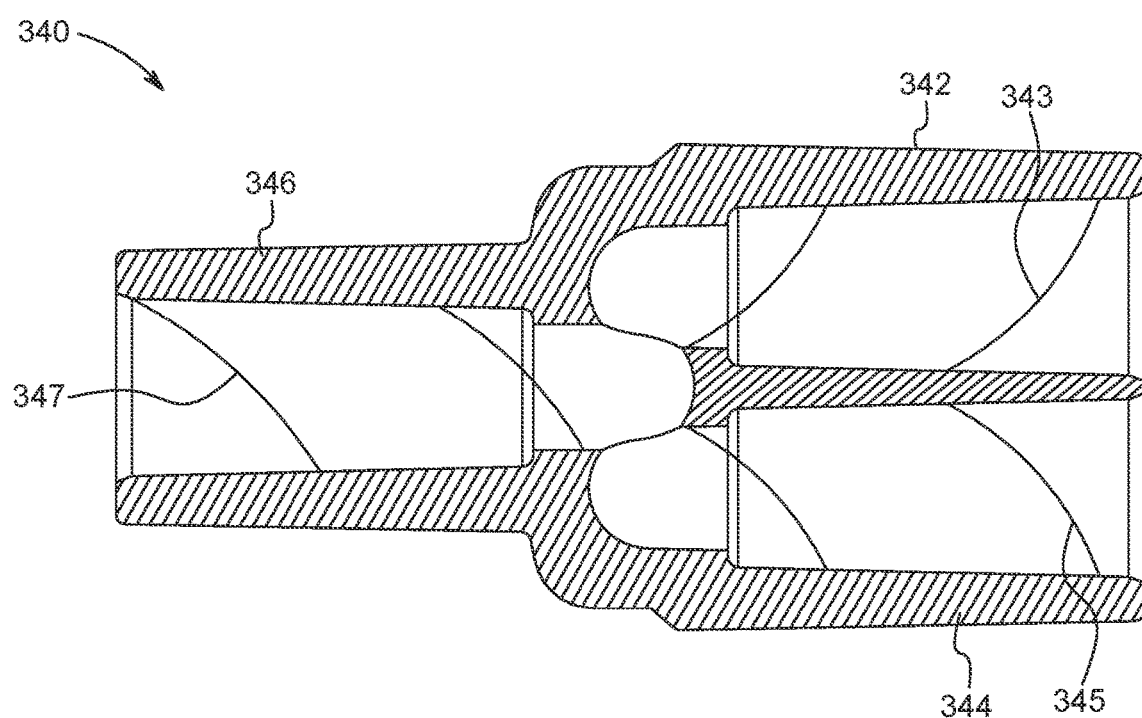
FIG. 7 is a cross-sectional view of a fluid mixing device according to another embodiment of the present disclosure.

FIG. 7 is a section view of another embodiment of the fluid mixing device 340, according to another example of the present disclosure where at least one of the first fluid inlet 342, the second fluid inlet 344, and the outlet port 346 include a helical "rifling" pattern on an inner surface to further direct and rotate the respective fluid flow in the inlet and/or outlet and increase turbulent mixing of the first and second fluids. The pattern may include one or more at least partially helical protrusions or indentations recessed into the inner surface or protruding from the inner surface of at least one of the first fluid inlet 342, the second fluid inlet 344, and the outlet port 346. The pattern imparts a rotation of the flow of the fluid within the corresponding fluid path. In the example of FIG. 7, the first fluid inlet 342, the second fluid inlet 344, and the outlet port 346 each have an at least partially helical-shaped portion 343, 345, and 347 for generating a corresponding fluid vortex for at least one of the first injection fluid, the second injection fluid, and the mixture of the first and second injection fluids, respectively, as the respective fluids flow through the channels. The helical-shaped portion in one of the inlets or outlet may have directionality (clockwise or counterclockwise) in the same or different direction and may have different dimensions or pitch as the helical-shaped portion in the other portions of the mixing device 340. Although the first and second fluid inlets 342 and 344 and the outlet port 346 each have helical-shaped portions 343, 345, and 347, it will be appreciated that any number of the aforementioned regions may be provided with a helical-shaped portion, without departing from the scope of the disclosed concept. By having the helical-shaped portions 343, 345, and 347, mixing may advantageously be further improved. It will be appreciated that the fluid mixing device 340 otherwise functions the same as the fluid mixing device 240 discussed above.

Figure 8:
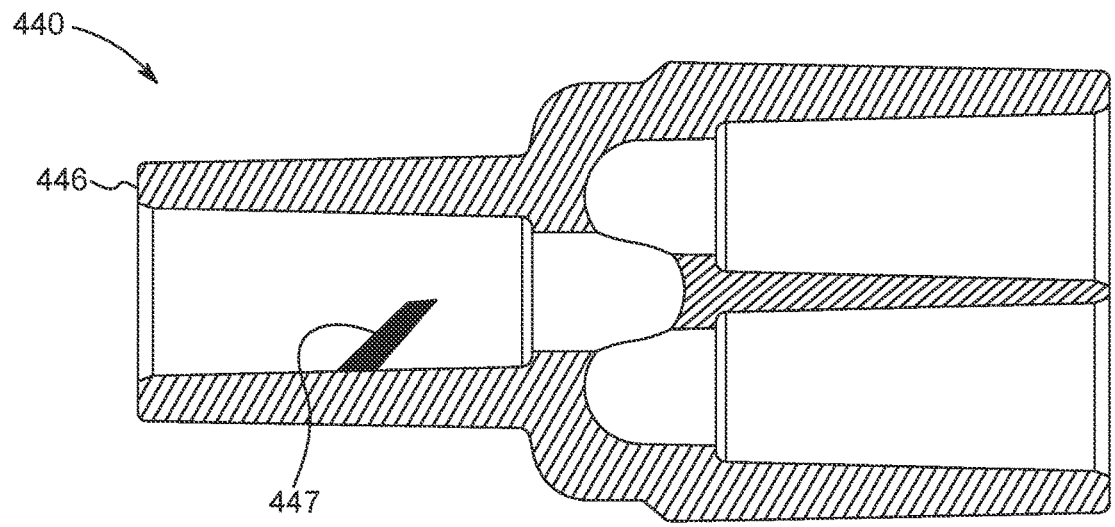
FIG. 8 is a cross-sectional view of a fluid mixing device according to another embodiment of the present disclosure.

In another embodiment of a fluid mixing device 440 of the present disclosure, as shown in FIG. 8, the outlet port 446 of the fluid mixing device 440 may have one or more baffle members or mixing members 447 located on an interior thereof. The baffle member 447 may advantageously further improve mixing of the first and second injection fluids. It will be appreciated that the fluid mixing device 440 otherwise functions the same as the fluid mixing device 240, discussed above. In other embodiments, the fluid mixing device may include one or more baffle member or mixing member in one or both of the first and second fluid inlets.

Figure 9:
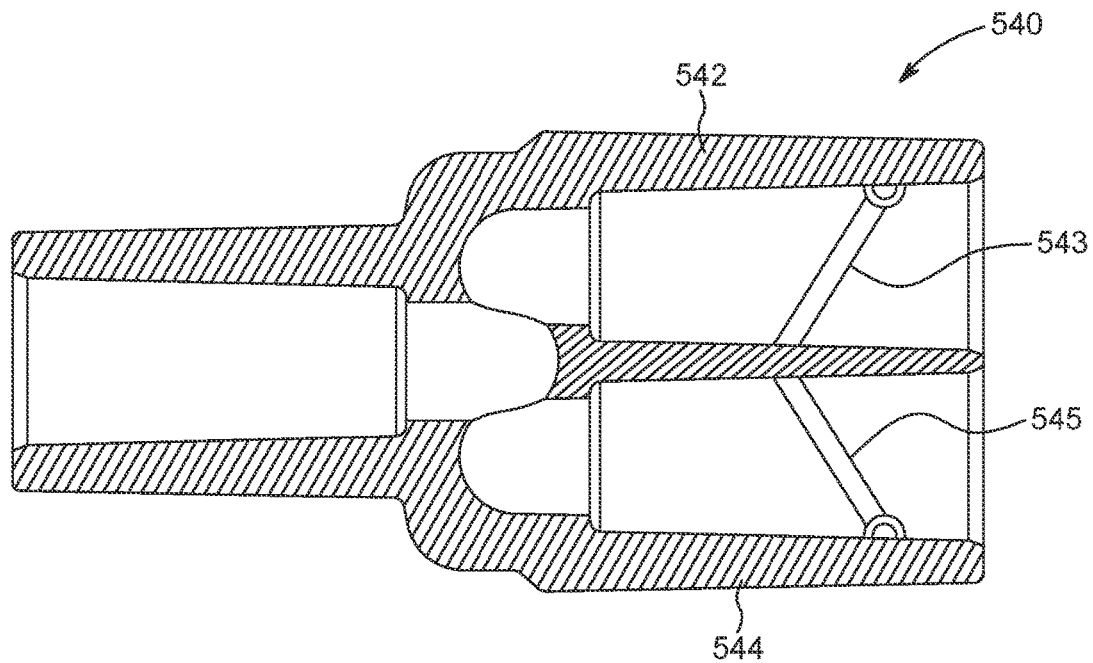
FIG. 9 is a cross-sectional view of a fluid mixing device according to another embodiment of the present disclosure.

FIG. 9 shows yet a further example of a fluid mixing device 540, in accordance with another embodiment of the present disclosure. As shown, the fluid mixing device 540 may include a first valve 543 in the first fluid inlet 542 configured to prevent backflow of the second injection fluid into the first fluid inlet 542 and fluid line 217*a*. Furthermore, the fluid mixing device 540 may include a second valve 545 in the second fluid inlet 544 configured to prevent backflow of the first injection fluid into the second fluid inlet 544 and fluid line 217*b*. Under the injection pressures typical of a fluid injection procedure, when the pressure of one fluid in the upstream fluid path and fluid inlet is greater than the pressure of the other fluid in the upstream other fluid path and other fluid inlet, backflow of the fluid under greater pressure into the lower pressure fluid path may result in undesired mixing of the fluids in the upstream fluid path or other upstream components of the fluid injection system. This may lead to inaccurate dosing of contrast agent due to the undesired mixing of the two fluid prior to the controlled mixing in the fluid mixing device and may lead to decreased image quality and exposure of the patient to unnecessary excess contrast agent. Otherwise, the fluid mixing device 540 functions the same as the fluid mixing device 240.

Figure 10:
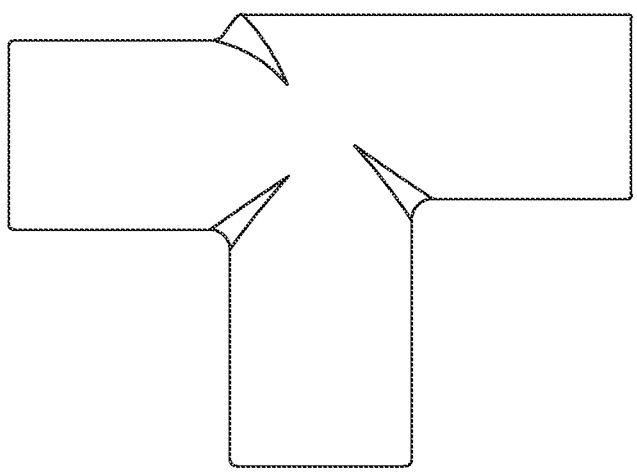
FIG. 10 is a top view of a fluid mixing device according to another embodiment.
Figure 11:
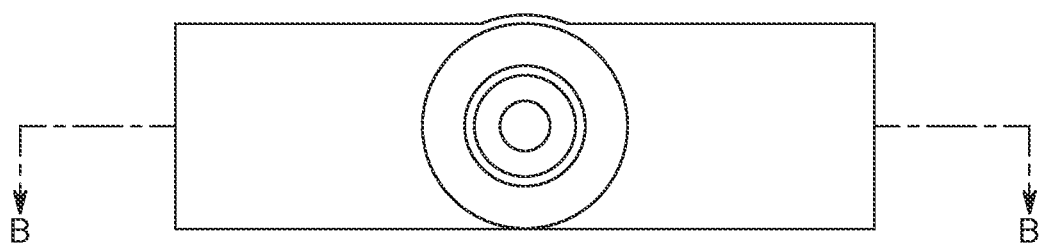
FIG. 11 is a side view of the fluid mixing device shown in FIG. 10.
Figure 12:
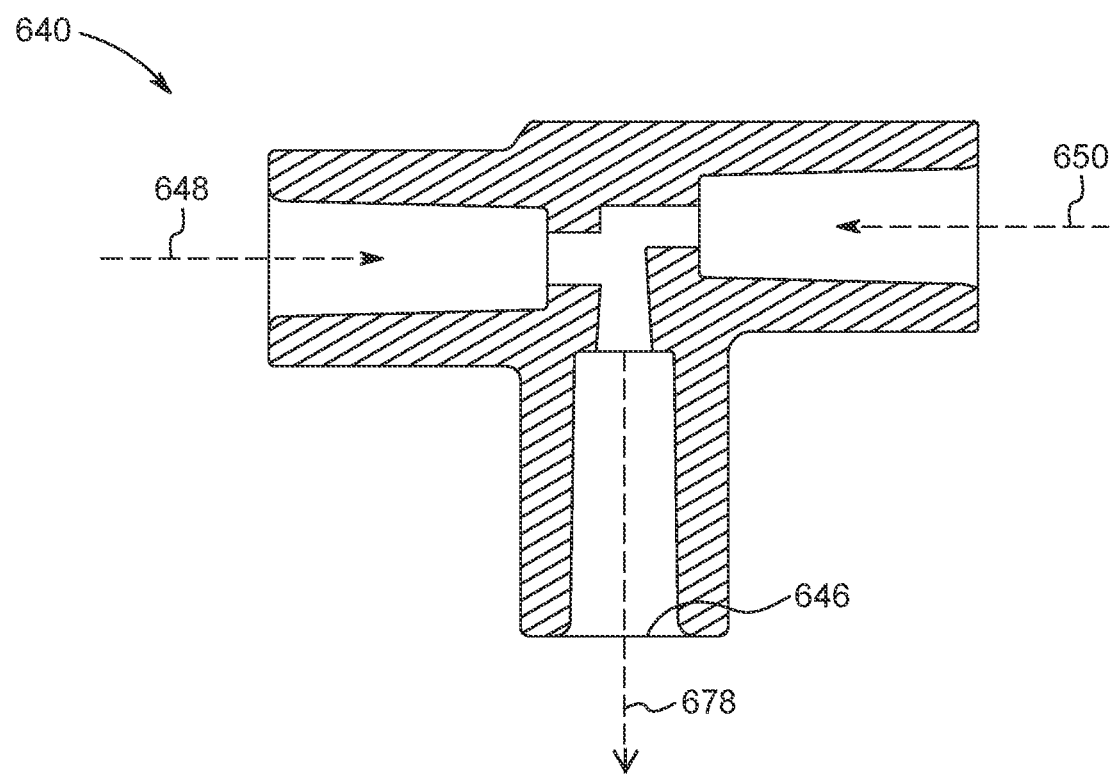
FIG. 12 is a cross-sectional view of the fluid mixing device of FIGS. 10-11, taken along line B-B in FIG. 11.

In another embodiment of a fluid mixing device 640 of the present disclosure, as shown in FIGS. 10-12, the first direction 648 (FIG. 12) is parallel to, in the opposite direction from, and offset from the second direction 650 (FIG. 12). Furthermore, as shown, the outlet port 646 of the fluid mixing device 640 has an axis 678 generally perpendicular to the first and second directions 648 and 650. Accordingly, the fluid mixing device 640 provides indirect instead of head-on mixing of the two fluids. For example, the first direction 648 and the second direction 646 facilitate a direct collision of stream lines of one-half the diameter of the tubing cross-section and indirect mixing of the other one-half of the stream lines. That is, because of the offset of the two opposing fluid directions 648 and 650, half direct mixing and half indirect mixing occurs in the fluid mixing region.

Figure 13:
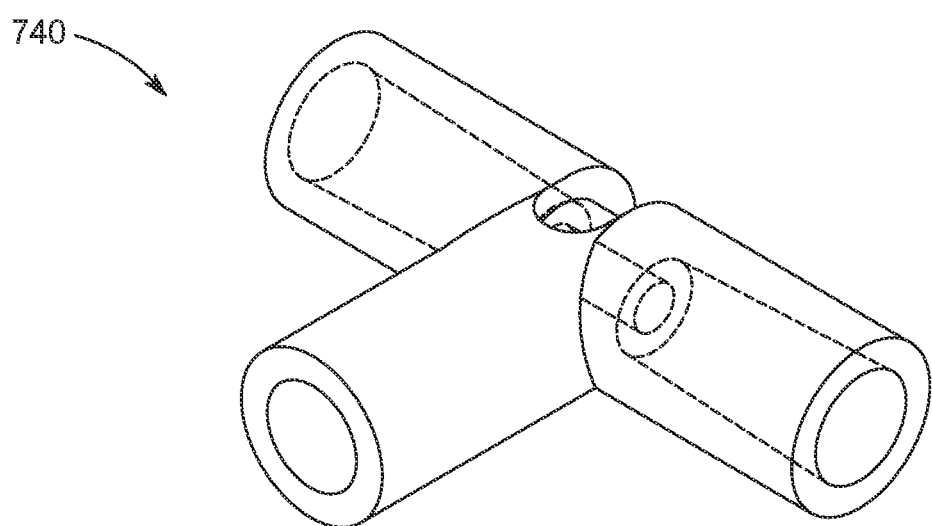
FIG. 13 is a perspective view of a fluid mixing device according to another embodiment.
Figure 14:
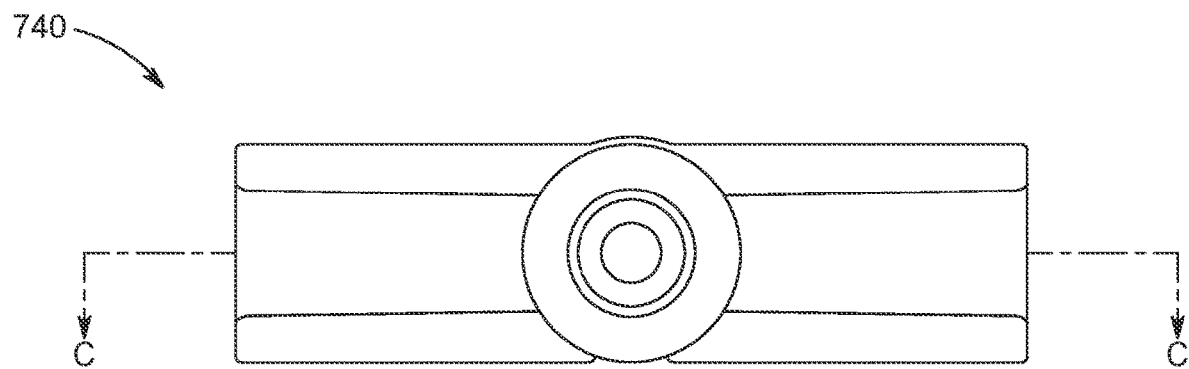
FIG. 14 is a side view of the fluid mixing device shown in FIG. 13.
Figure 15:
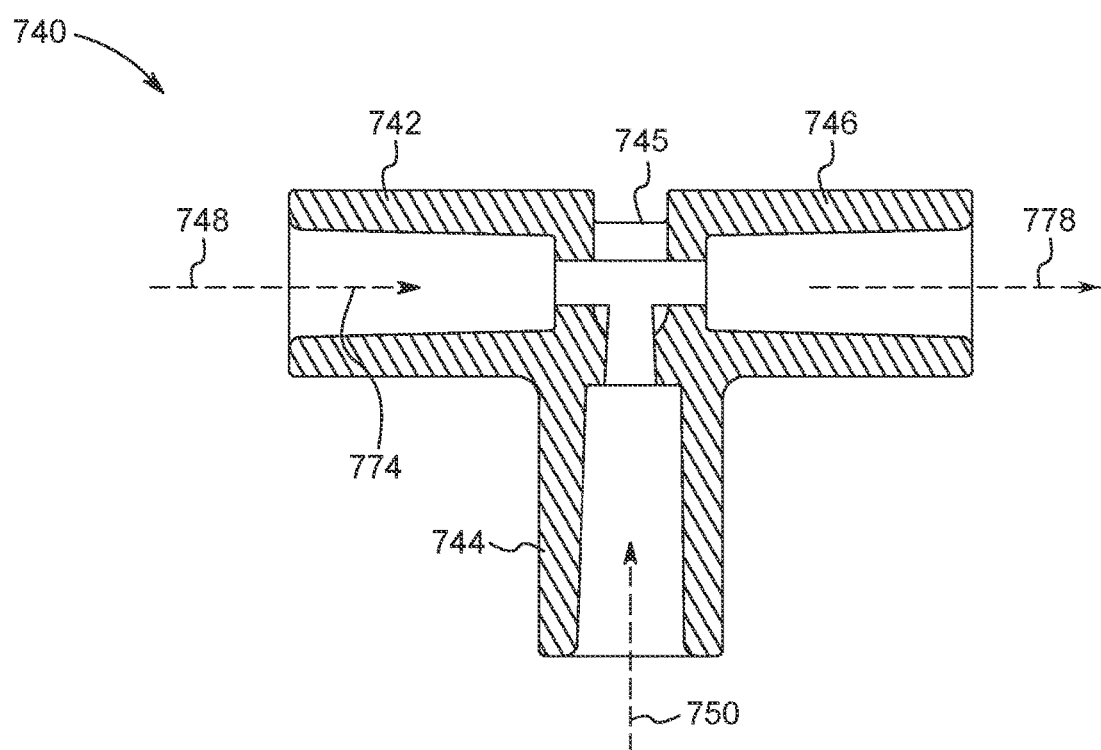
FIG. 15 is a cross-sectional view of the fluid mixing device of FIGS. 13-14, taken along line C-C in FIG. 14.

In yet another embodiment of a fluid mixing device 740 of the present disclosure, as shown in FIGS. 13-15, the first direction 748 is generally perpendicular to the second direction 750. Moreover, the outlet port 746 of the fluid mixing device 740 may have an axis 778 generally parallel and coincidental to an axis 774 of the first fluid inlet 742. In an alternative embodiment, fluid mixing device 740 (not shown) may have an axis 778 of an outlet port 746 generally parallel and coincidental to an axis of a second fluid inlet 744. At least one notch 745 may be provided between two of the first fluid inlet 742, the second fluid inlet 744, and the outlet port 746. The notch 745 may be provided to conserve material in a transition area between two of the first fluid inlet 742, the second fluid inlet 744, and the outlet port 746 to facilitate molding of the fluid mixing device 740. According to these embodiments, the perpendicular collision of the flow paths of the first fluid and the second fluid in the fluid mixing device 740 may create turbulent mixing of the two fluids and limit and/or disrupt any laminar flow of one fluid relative to the other fluid.

Figure 16:
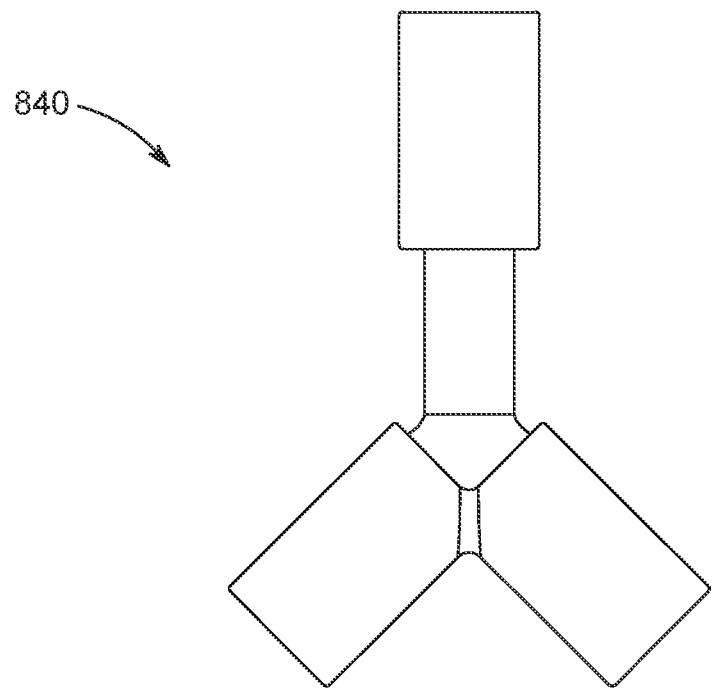
FIG. 16 is a top view of a fluid mixing device according to another embodiment of the present disclosure.
Figure 17:
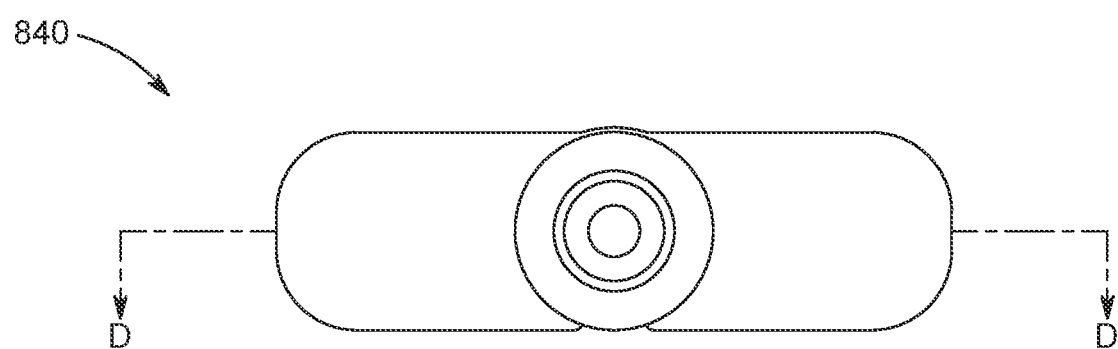
FIG. 17 is a top view of the fluid mixing device shown in FIG. 16.
Figure 18:
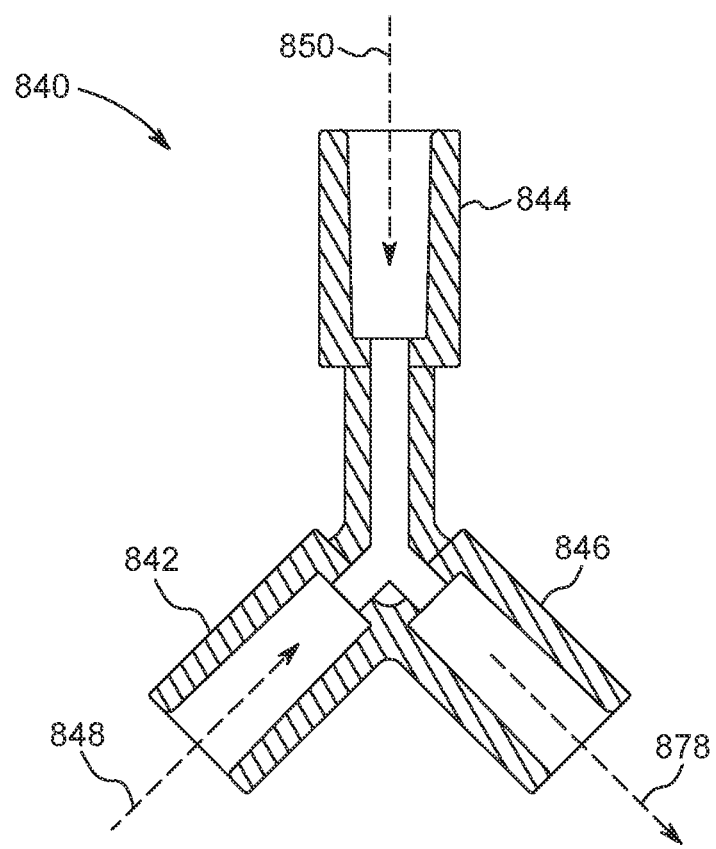
FIG. 18 is a cross-sectional view of the fluid mixing device of FIGS. 16-17, taken along line D-D in FIG. 17.

In yet another embodiment of a fluid mixing device 840 of the present disclosure, as shown in FIGS. 16-18, the first direction 848 may be at an angle of between 130° and 165° with respect to the second direction 850. Additionally, the outlet port 846 of the fluid mixing device 840 may have an axis 878 at an angle less than 70° with respect to the first direction 848. In an alternative embodiment, fluid mixing device 840 (not shown), the outlet port 846 may have an axis 878 at an angle less than 70° with respect to second direction 850. According to these embodiments, the angled but substantially opposite flow of the flow paths of the first fluid and the second fluid in fluid mixing device 840 may create turbulent mixing of the two fluids and limit and/or disrupt any laminar flow of one fluid relative to the other fluid.

Figure 19:
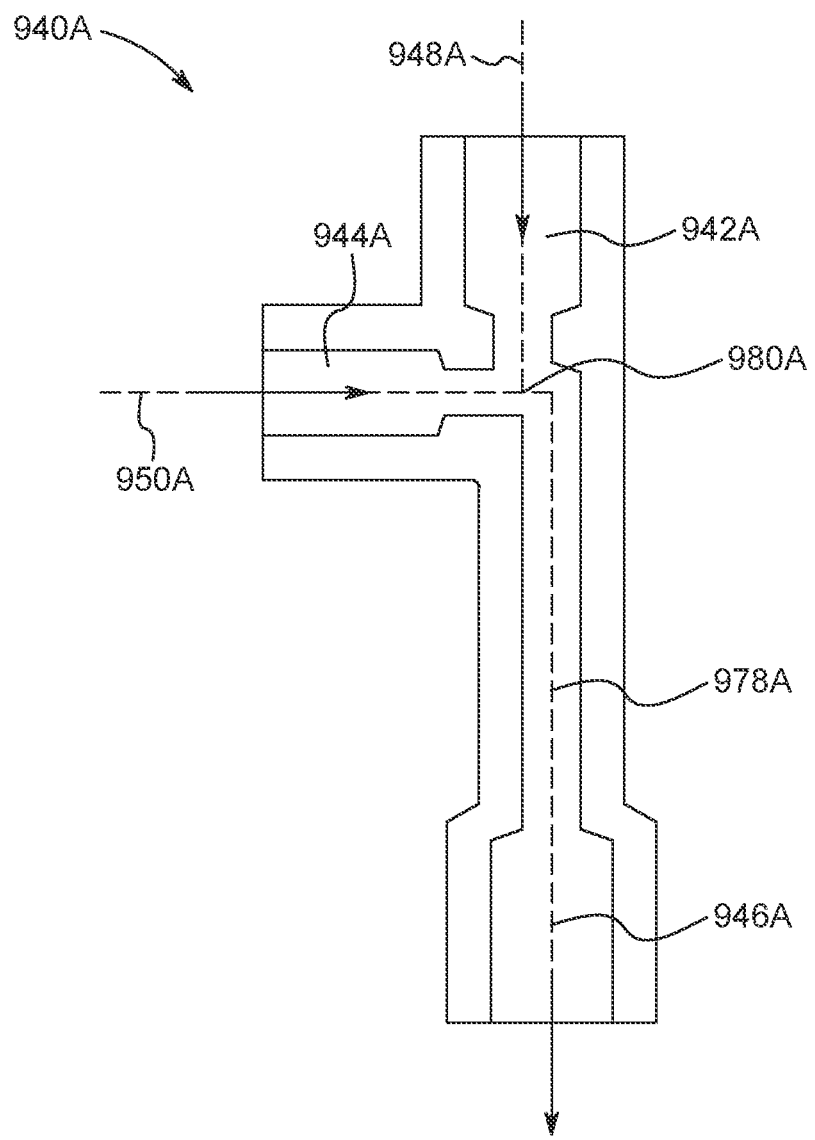
FIGS. 19-21 are a cross-sectional views of fluid mixing devices according to further embodiments of the present disclosure.
Figure 20:
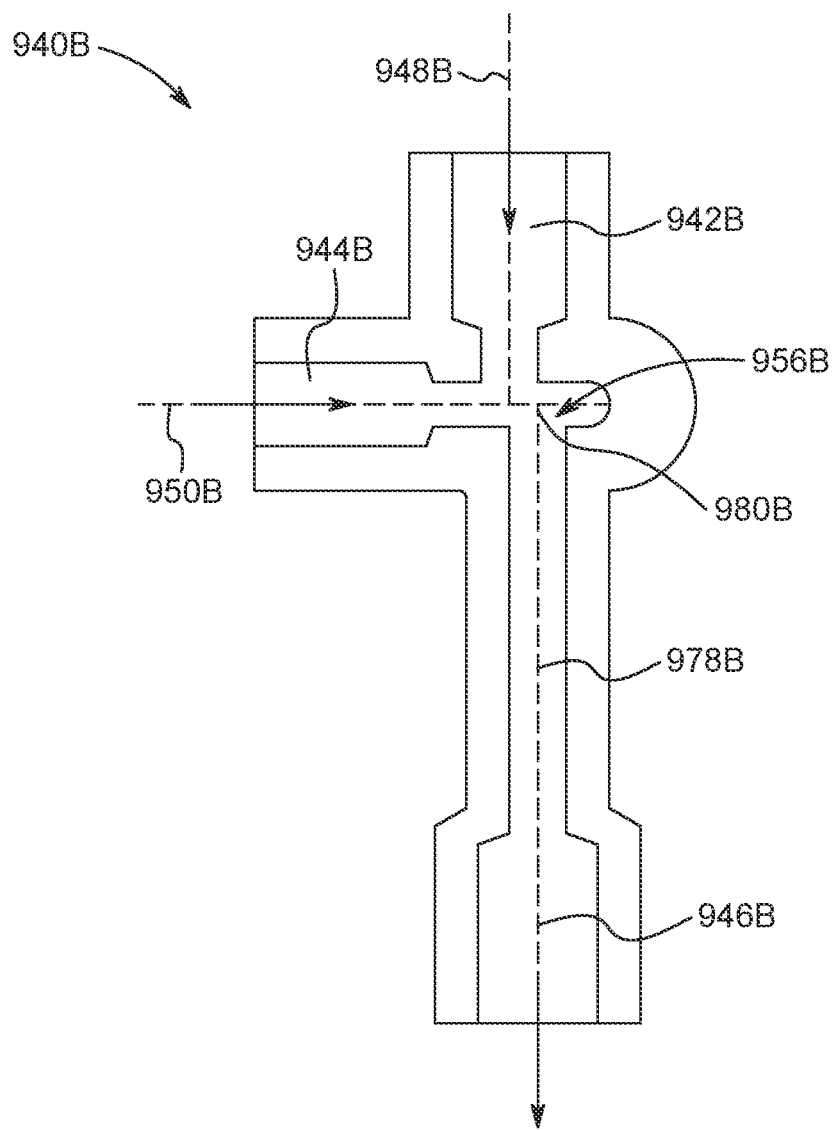
Figure 21:
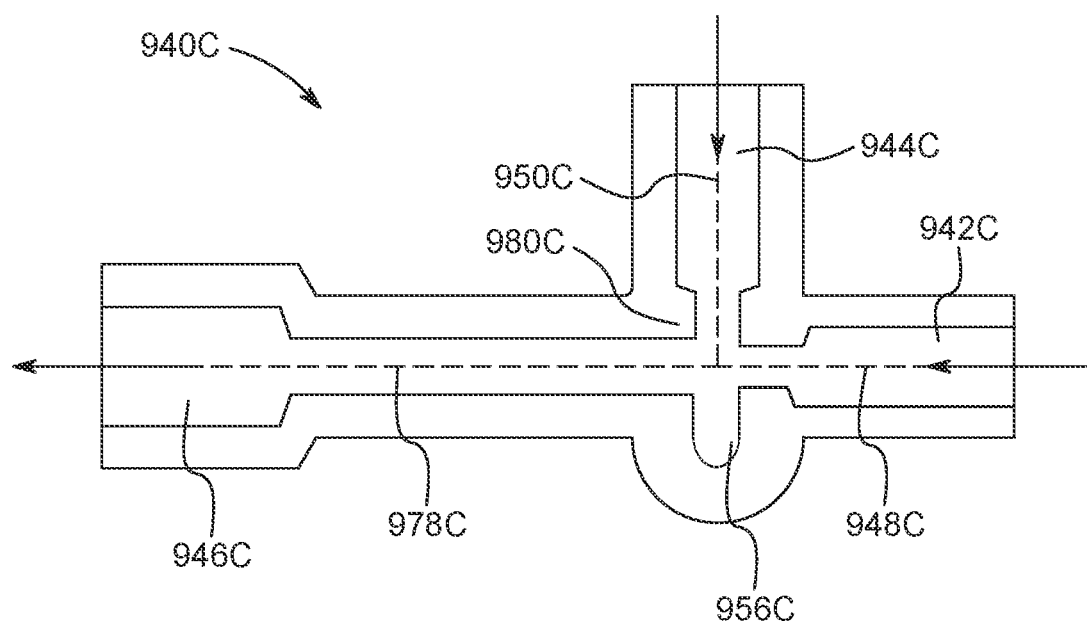

Other examples of fluid mixing devices 940A, 940B, and 940C, in accordance with various embodiments of the present disclosure, are shown in FIGS. 19-21. According to these embodiments, the fluid mixing device 940A, 940B, and 940C has a T-shaped 90 degree connector design having one or more offset fluid paths to enhance mixing of the first fluid and the second fluid. Referring first to FIG. 19, fluid mixing device 940A includes a first fluid inlet 942A and a second fluid inlet 944A for a first fluid and a second fluid respectively, and a fluid outlet 946A. As can be seen in FIG. 19 the first fluid flow axis 948A is offset from both the second fluid flow axis 950A and the fluid outlet flow axis 978A. Fluid mixing occurs at least in fluid mixing region 980A where offset fluid flow lines of the first fluid along axis 948A interact with fluid flow lines of the second fluid line along axis 950A to create a turbulent mixing in fluid mixing region 980A, which may be further enhanced by the offset of the outlet flow axis 978A to the fluid outlet 946A.

Referring to FIG. 20, fluid mixing device 940B includes a first fluid inlet 942B and a second fluid inlet 944B for a first fluid and a second fluid respectively, and a fluid outlet 946B. The fluid mixing device 940B also includes a turbulent fluid mixing chamber 956B where further turbulent mixing may occur. As can be seen in FIG. 20 the first fluid flow axis 948B is offset from both the second fluid flow axis 950B and the fluid outlet flow axis 978B. Fluid mixing occurs at least in fluid mixing region 980B where the fluid mixing chamber 956B and the offset fluid flow lines of the first fluid along axis 948B interact with fluid flow lines of the second fluid line along axis 950B to create a turbulent mixing in fluid mixing region 980B, which may be further enhanced by the offset of the outlet flow axis 978B to fluid outlet 946B.

Referring to FIG. 21, fluid mixing device 940C includes a first fluid inlet 942C and a second fluid inlet 944C for a first fluid and a second fluid respectively, and a fluid outlet 946C. The fluid mixing device 940C also includes a turbulent fluid mixing chamber 956C where further turbulent mixing may occur. As can be seen in FIG. 21 the first fluid flow axis 948C is offset from and the fluid outlet flow axis 978C, particularly on the side of the flow path opposite the second fluid inlet 944C. Fluid mixing occurs at least in fluid mixing region 980C where the fluid mixing chamber 956C and the fluid flow lines of the first fluid along axis 948C interact with fluid flow lines of the second fluid line along axis 950C to create a turbulent mixing in fluid mixing region 980C, which may be further enhanced by the offset of the outlet flow axis 978C to the fluid outlet 946C.

Figure 22:
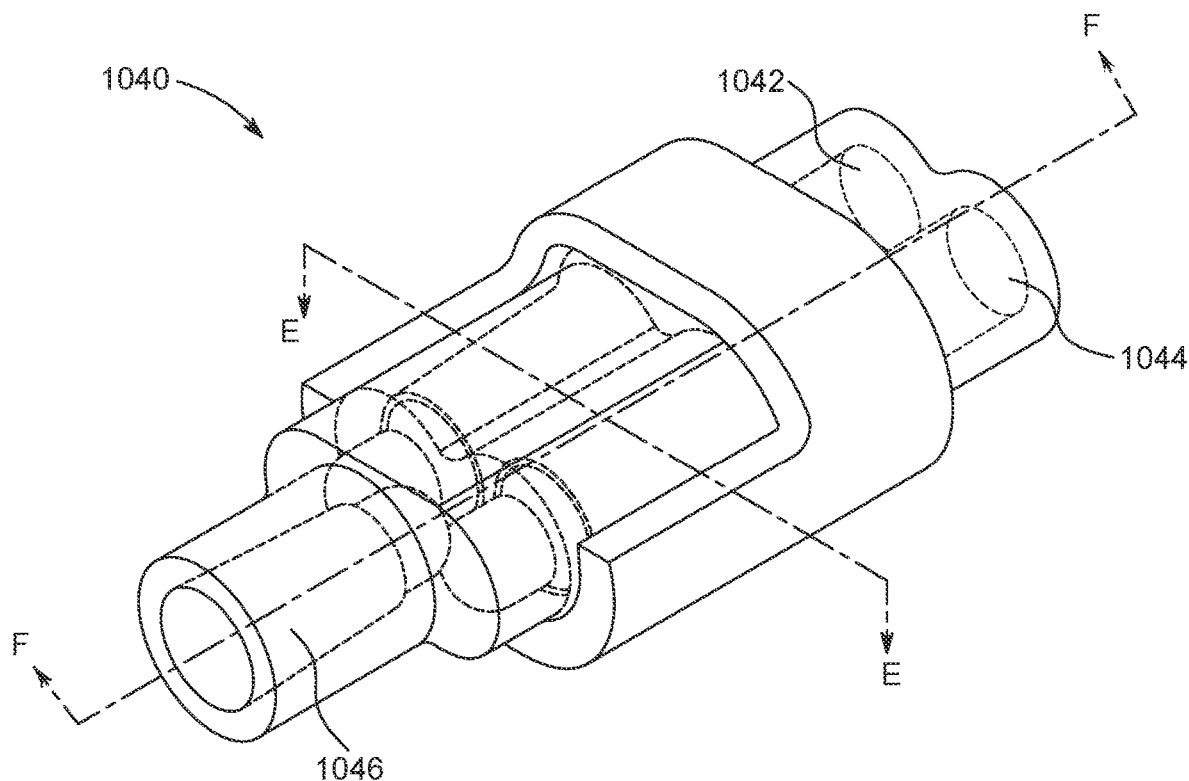
FIG. 22 is a perspective view of a fluid mixing device according to another embodiment.

FIG. 22 is a perspective view of a fluid mixing device 1040 according to some non-limiting embodiments of the present disclosure. The fluid mixing device 1040 may be used as part of a fluid delivery tube set, such as the fluid delivery tube set 202 shown in FIG. 2, wherein the fluid mixing device 1040 is connected to a pair of fluid inlet lines and an outlet line. As shown in FIG. 22, the fluid mixing device 1040 has a body defining first and second fluid inlets 1042 and 1044, each of which is configured to conduct a corresponding one of the first and second injection fluids. The fluid mixing device 1040 further has an outlet port 1046 that is configured for delivering a mixture of the first and second injection fluids from the fluid mixing device 1040 to the patient or other downstream fluid path component.

Figure 23:
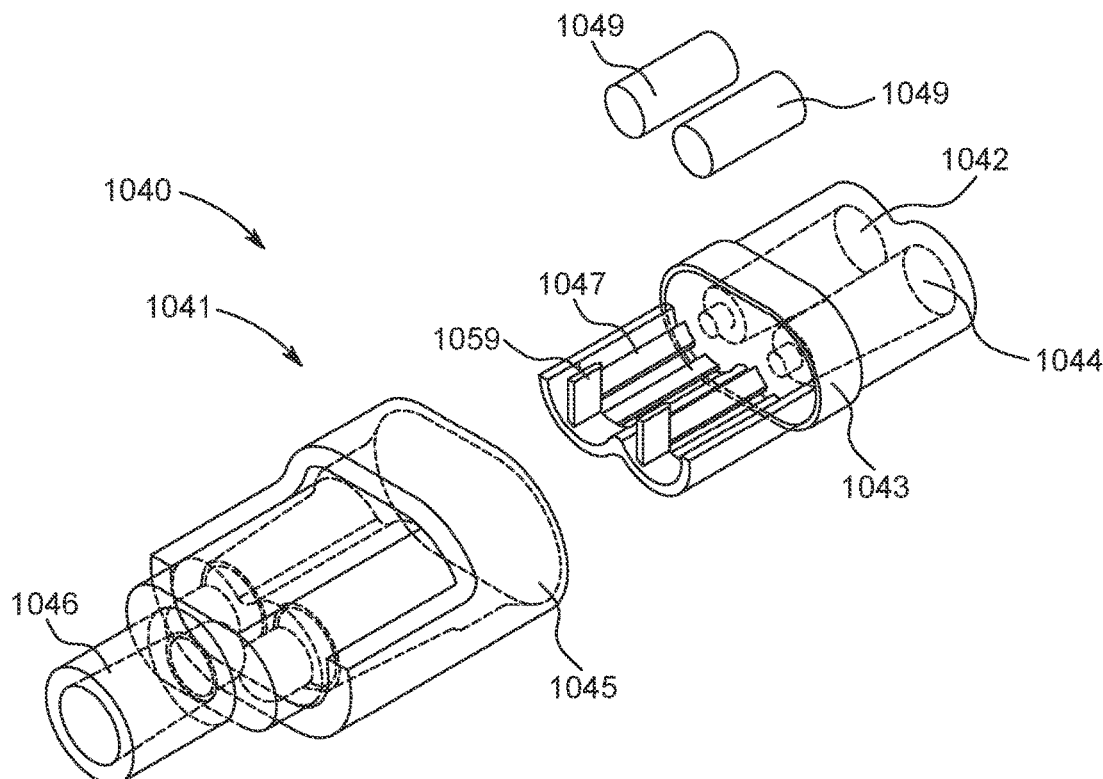
FIG. 23 is an exploded view of a fluid mixing device shown in FIG. 22.

With reference to FIG. 23, which is an exploded perspective view of the fluid mixing device 1040 shown in FIG. 22, the fluid mixing device 1040 has a body 1041 with a first portion 1043 and a second portion 1045. In some embodiments, the first portion 1043 and the second portion 1045 may be manufactured separately and are connected together to form the body 1041 of the fluid mixing device 1040. Desirably, the first portion 1043 and the second portion 1045 are connected together in a non-removable manner, such as by adhesive, welding (e.g., laser welding or ultrasonic welding), friction fit, solvent gluing, or other non-removable connection mechanism. In some embodiments, the first portion 1043 and the second portion 1045 may be removably connected together.

With continued reference to FIG. 23, the first portion 1043 defines a portion of the first and second fluid inlets 1042 and 1044, and has a receiving cavity 1047 for receiving a check valve 1049 in each of the first and second fluid inlets 1042 and 1044. The second portion 1045 has a corresponding inner cavity 1051 (shown in FIG. 24A) that is configured to receive the first portion 1043, including the check valves 1049. A second part of the first and second fluid inlets 1042 and 1044 is defined by the inner cavity 1051 of the second portion 1045 (shown in FIGS. 24A-24B). Once the first portion 1043, including the check valves 1049, is inserted into the second portion 1045, the first portion 1043 and the second portion 1045 may be joined together at one or more contact points between the first portion 1043 and the second portion 1045.

Each check valve 1049 may be configured to prevent backflow of the first and second injection fluids during injection procedures where fluid pressures in the respective first and second tubes delivering the first and second injection fluids to the fluid mixing device 1040 are not equal. The check valves 1049 may be made from a compressible material, such as an elastomeric polymer, that may be compressed under the pressurized flow of the fluid from an expanded state to a compressed state. The compressible material may be selected as appropriate to provide the appropriate stiffness so that the check valve opens at a selected fluid pressure. The check valves 1049 may also be used to isolate the fluid injector system from dampening a hemodynamic blood pressure signal, as discussed herein with reference to FIGS. 28-30. In some embodiments, the check valves 1049 may be used to isolate contamination from patient to patient when the fluid mixing device 1040 is configured for multi-patient use. Furthermore, the check valves 1049 prevent "dribbling" of the first and second injection fluids to the outlet after the injection of first and second injection fluids ceases, such as due to release of built-up capacitance or "swelling" of the fluid injector components under pressure.

Figure 24A:
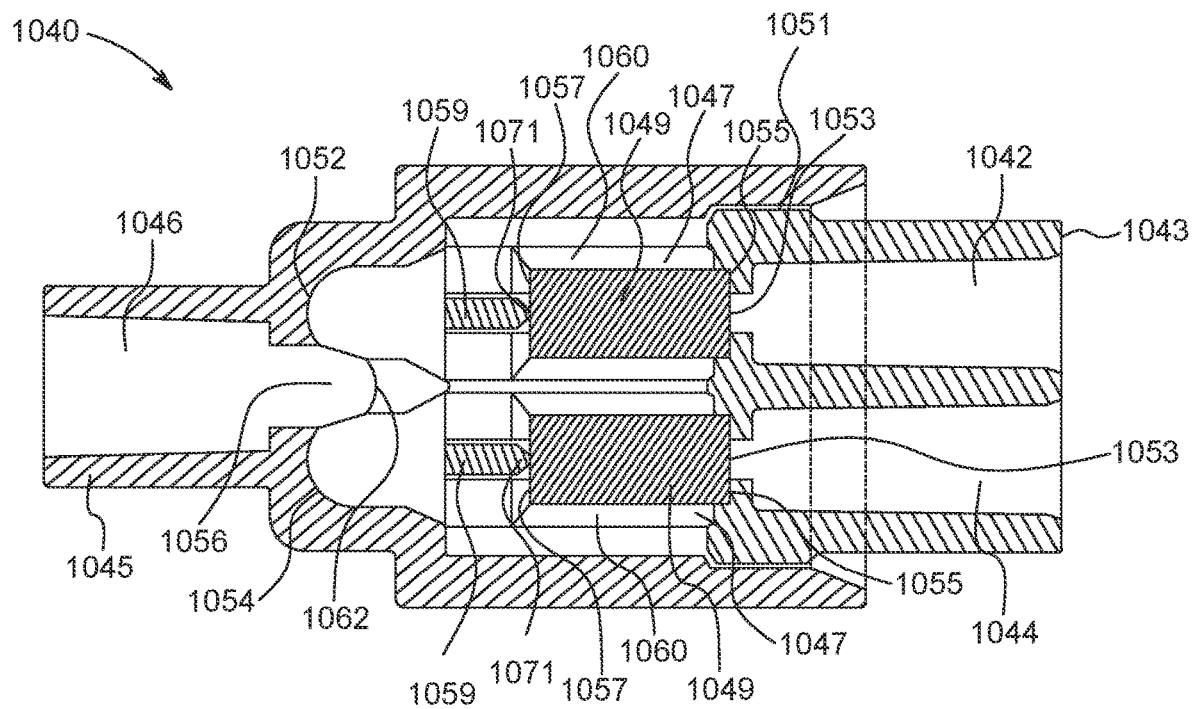
FIG. 24A is a cross-sectional view of the fluid mixing device of FIGS. 22-23, taken along line E-E in FIG. 22, with a check valve shown in a closed position.
Figure 24B:
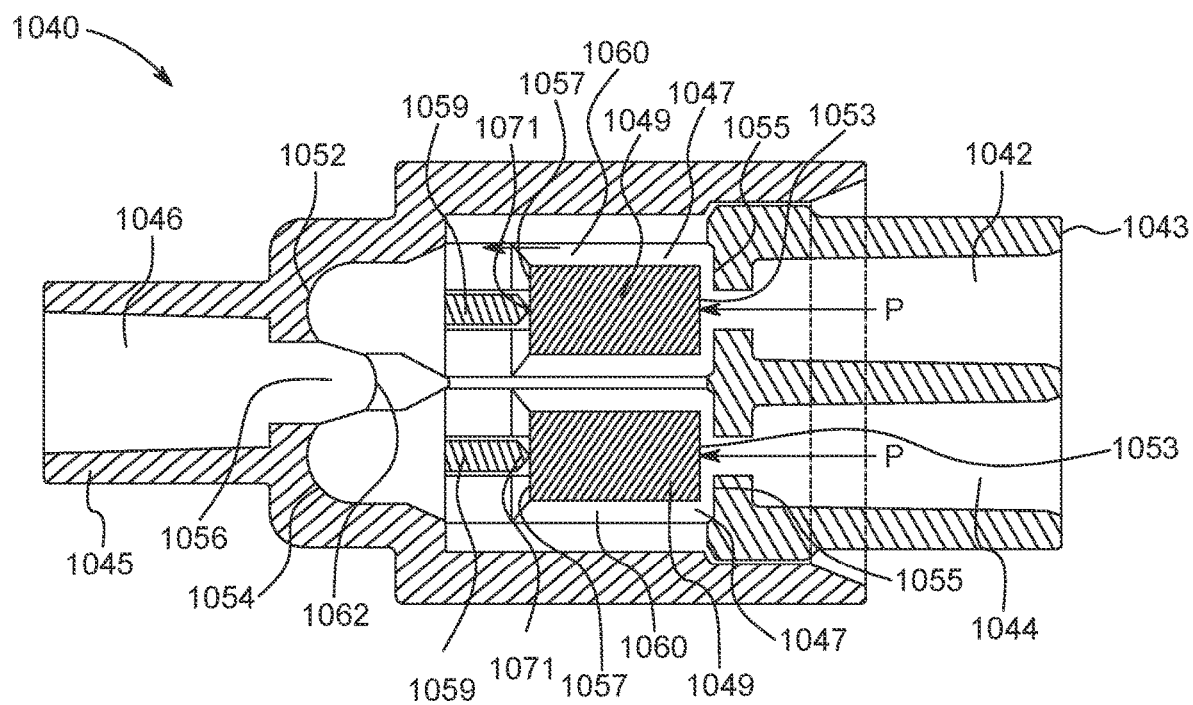
FIG. 24B is a cross-sectional view of the fluid mixing device of FIGS. 22-23, taken along line E-E in FIG. 22, with a check valve shown in an open position.

With reference to FIGS. 24A-24B, which show a cross-sectional plan view of the fluid mixing device 1040 taken along line F-F shown in FIG. 22, the check valves 1049 are shown positioned in the receiving cavity 1047 of each of the first and second fluid inlets 1042 and 1044 of the first portion 1043. The receiving cavity 1047 for each valve 1049 is aligned with a direction of fluid flow through each of the first and second fluid inlets 1042 and 1044. Each check valve 1049 has a proximal end 1053 that is configured to be in contact with a corresponding sealing face 1055 on the first and second fluid inlets 1042 and 1044 in the first portion 1043 when the check valve 1049 is in a closed position (FIG. 24A), and that is configured to be spaced apart from the sealing face 1055 on the first and second fluid inlets 1042 and 1044 in the first portion 1043 when the check valve 1049 is in an open position (FIG. 24B). Each check valve 1049 further has a distal end 1057 that is engaged with a stop element 1059 positioned within each of the first and second fluid inlets 1042 and 1044. In some embodiments, each stop element 1059 may be a support structure that is connected to an inner sidewall of the respective first and second fluid inlet 1042, 1044 downstream of the check valve 1049 and is configured to prevent movement of the distal end 1057 of the check valve 1049, thus allowing the check valve 1049 to compress when subject to a pressure force on the proximal end 1053. In some embodiments, each stop element 1059 may have a pointed proximal end 1071 that is configured to reduce the contact area with the check valve 1049, thereby allowing for a greater compression of the check valve 1049 between its proximal and distal ends 1053 and 1057 at a lower fluid pressure. For example, under pressure, the distal end 1057 may compress and mold around the pointed proximal end 1061 of the stop element 1059 allowing the outer circumference of the proximal end 1053 to more readily release from the sealing face 1055. In this manner, the pointed stop element 1059 allows for decreased pressure drops by allowing easier opening during injections compared to stop elements with a flat supporting surface. In some embodiments, stop element 1059 is made from a silicone material.

During an injection procedure, the first and second injection fluids are urged under pressure through the first and second fluid inlets 1042 and 1044 such that the first and second fluids engage respective proximal ends 1053 of the check valves 1049. Initially, the proximal ends 1053 engage the sealing face 1055 on the first portion 1043 (FIG. 24A) to block the passage of the first and second injection fluids past the check valve 1049. As the fluid pressure builds, the force on the proximal end 1053 of the check valves 1049 increases. Due to the compressible nature of each check valve 1049, the proximal end 1053 is urged in the distal direction, thereby creating a gap between the proximal end 1053 of the check valves 1049 and the sealing face 1055 on the first portion 1043. As shown in FIG. 24B, such a gap is formed only when sufficient fluid pressure P is imparted on the proximal end 1053, such as, for example, during a typical injection procedure. The pressurized first and second injection fluids then travel around the respective check valves 1049 and through the fluid mixing device 1040, as described herein. During the injection procedure, if the pressure of one of the first and second injection fluids is higher than the pressure of the other of the first and second injection fluids, the check valve 1049 in the fluid inlet with the lower pressure may close to prevent a backflow of the fluid in an upstream direction, for example due to the back pressure of the higher pressure fluid on the distal end 1055 of the lower pressure check valve 1049. After the injection procedure is completed, the resilient nature of each check valve 1049 causes the check valve 1049 to expand axially such that the proximal end 1053 engages the sealing face 1055 on the first portion 1043 to prevent additional fluid from flowing past the check valve 1049. In this manner, any excess fluid is prevented from flowing through the fluid mixing device 1040 after the completion of the injection procedure. Further, any backflow of one fluid into the other fluid path is prevented.

Figure 25:
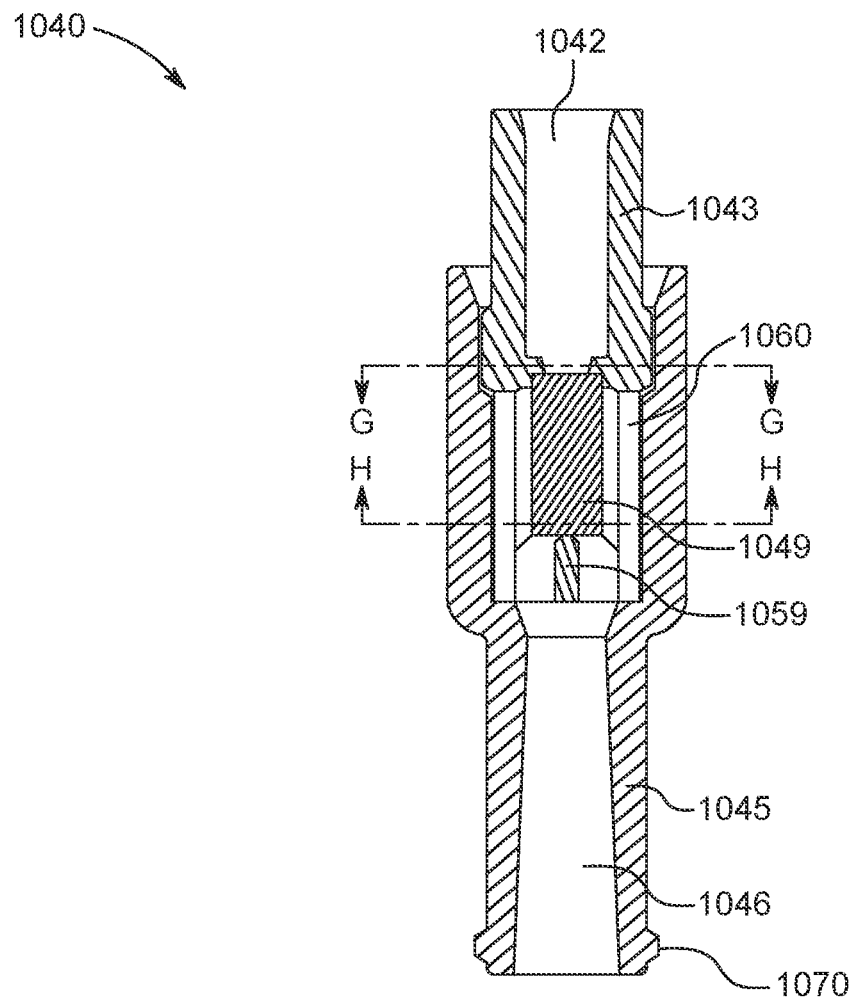
FIG. 25 is a cross-sectional view of the fluid mixing device of FIGS. 22-23, taken along line F-F in FIG. 22.
Figure 26:
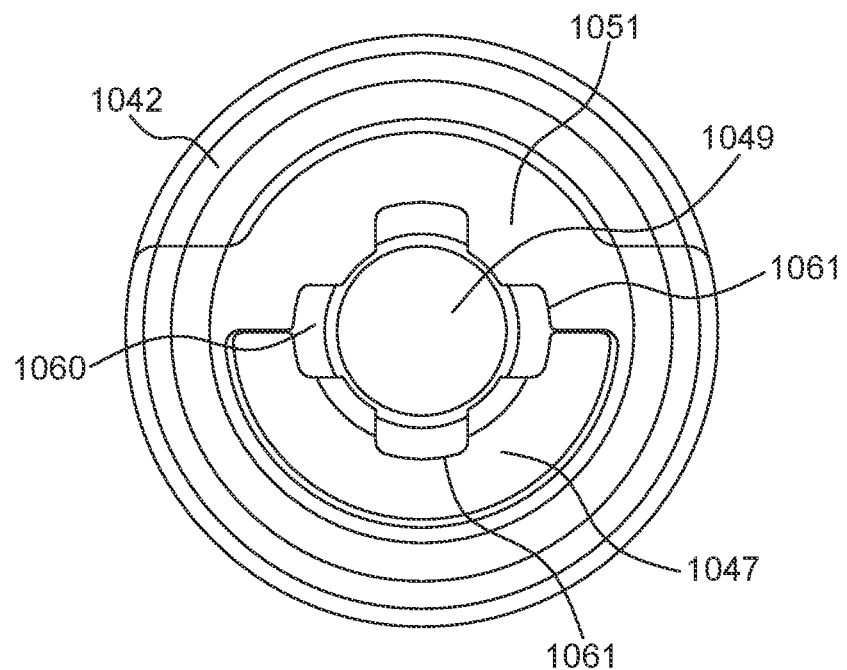
FIG. 26 is a cross-sectional view of a fluid inlet of the fluid mixing device shown in FIG. 25 taken along line G-G in FIG. 25.

With reference to FIG. 25, and with continued reference to FIGS. 24A-24B, each check valve 1049 is dimensioned such that its outer diameter is slightly smaller than an inner diameter of a channel 1060 defined by the receiving cavity 1047 of the first portion 1043 (shown in FIGS. 23A-24B) and the corresponding inner cavity 1051 of the second portion 1045 of the body 1043 (shown in FIG. 26). In this manner, fluid may pass around the body of each check valve 1049 and through the channel 1060. In some embodiments, the channel 1060 may have a non-circular cross-section and the check valve 1049 may have a circular cross-section. In this manner, the channel 1060 defines a flow path for the first and second injection fluids to flow around the respective check valves 1049, when the check valve 1049 is in the open position.

In some embodiments, as shown in FIG. 26, the channel 1060 may have a fluted cross-section with one or more flutes 1061. In embodiments where the channel 1060 has a plurality of flutes 1061, the flutes 1061 may be spaced apart from each other at equal or unequal spacing about a perimeter of the channel 1060. The number of flutes 1061, the radial depth, and/or the circumferential width of the flutes 1061 may be selected based on a desired flow rate of the first and second fluids through the channel 1061 when the respective check valves 1049 are in the open position.

Each check valve 1049 is desirably an elastomeric part that is at least partially compressible in a longitudinal direction when acted upon by fluid pressure. The check valve 1049 in the first fluid inlet 1042 may be the same or different compared to the check valve 1049 in the second fluid inlet 1044. In some embodiments, the opening pressure of each check valve 1049 may be selected based on the characteristics of the fluid injector, and/or the characteristics of the first and second injection fluids, such as the fluid viscosity, and the temperature range, flow rate range, and the pressure range at which the first and second injections fluids will be injected.

Figure 27:
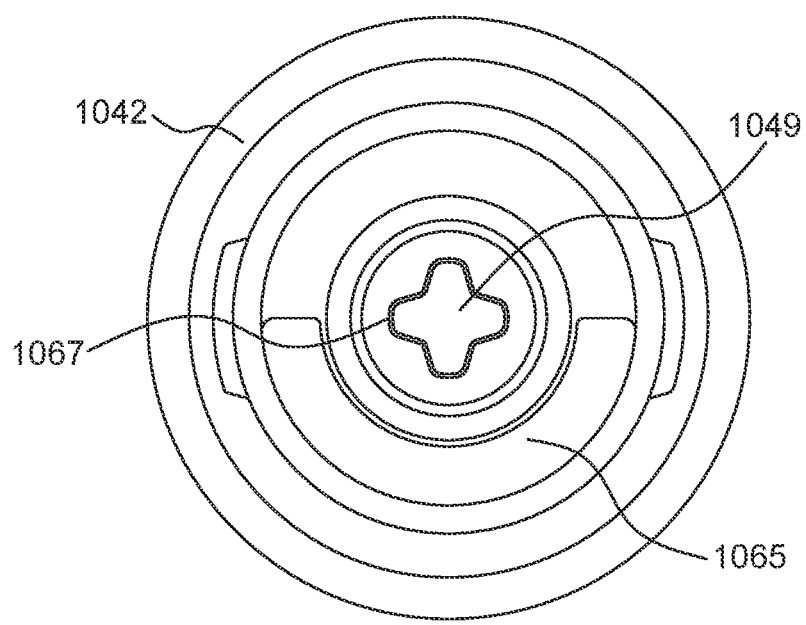
FIG. 27 is a cross-sectional view of the fluid inlet of the fluid mixing device shown in FIG. 25 taken along line H-H in FIG. 25.

With reference to FIG. 27, an inlet opening 1065 surrounding the sealing face 1055 (shown in FIG. 24A) may have a shape that corresponds to the shape of the channel 1060 (shown in FIG. 25). The inlet opening 1065 may have a taper 1067 that tapers radially inward in a direction from the proximal end toward the distal end of the fluid mixing device 1040. The cross-sectional shape of the inlet opening 1065 is chosen to achieve a low pressure drop and a lower opening pressure for the check valve 1049.

With reference to FIGS. 24A-24B, it will be appreciated that the fluid mixing device 1040 creates turbulent mixing of the first and second fluids similar to the fluid mixing device 240, discussed herein. As shown in FIGS. 24A-24B, the first and second fluid inlets 1042 and 1044 have corresponding first and second redirecting surfaces 1052 and 1054. Moreover, the fluid mixing device 1040 further has a mixing chamber 1056 in fluid communication with the first and second fluid inlets 1042 and 1044 and an outlet port 1046 in fluid communication with the mixing chamber 1056. The mixing chamber 1056 is configured to turbulently mix the first and second injection fluids together.

With continued reference to FIGS. 24A-24B, the first and second redirecting surfaces 1052 and 1054 are configured to redirect a first fluid and a second fluid entering the first and second fluid inlets 1042 and 1044, respectively, into the mixing chamber 1056, where the first and second injection fluids can then be turbulently mixed. As discussed herein with reference to FIG. 6, the first and second redirecting surfaces 1052 and 1054 are configured to redirect the first and second injection fluids in a corresponding first and second different directions that are different than the corresponding first and second directions in which the first and second injection fluids flow prior to contacting the first and second redirecting surfaces 1052 and 1054. Due to this deflection, the first and second injection fluids enter the mixing chamber 1056 along the corresponding first and second different directions and contact a third redirecting surface 1062 at a proximal end of the mixing chamber 1056 to turbulently mix the first and second injections fluids together in the mixing chamber 1056. After mixing, the mixture of the first and second injection fluids exits the fluid mixing device 1040 via the outlet port 1046 at a distal end of the fluid mixing device 1040.

With reference to FIG. 25, the outlet port 1046 may have a connection element 1070 configured for permitting removable connection of the outlet port 1046 with outlet tubing, such as the outlet line 220 shown in FIG. 2. The connection element 1070 may be a male luer lock that is configured to removably connect with a corresponding female luer lock on the proximal end of the outlet line 220. In some embodiments, the connection element 1070 may be a female luer lock that is configured to removably connect with a corresponding male luer lock on the proximal end of the outlet line 220. In other embodiments, fluid path connectors such as described in International PCT Application Nos. PCT/US2021/018523 and PCT/US2016/063448, the disclosures of which are incorporated by this reference. In this manner, the fluid mixing device 1040 can be removably connected to an outlet line 220 to thereby permit the use of the fluid mixing device 1040 with multiple patients, for example if one or more check valves are attached upstream of the connector on the outlet port 1046.

Figure 28:
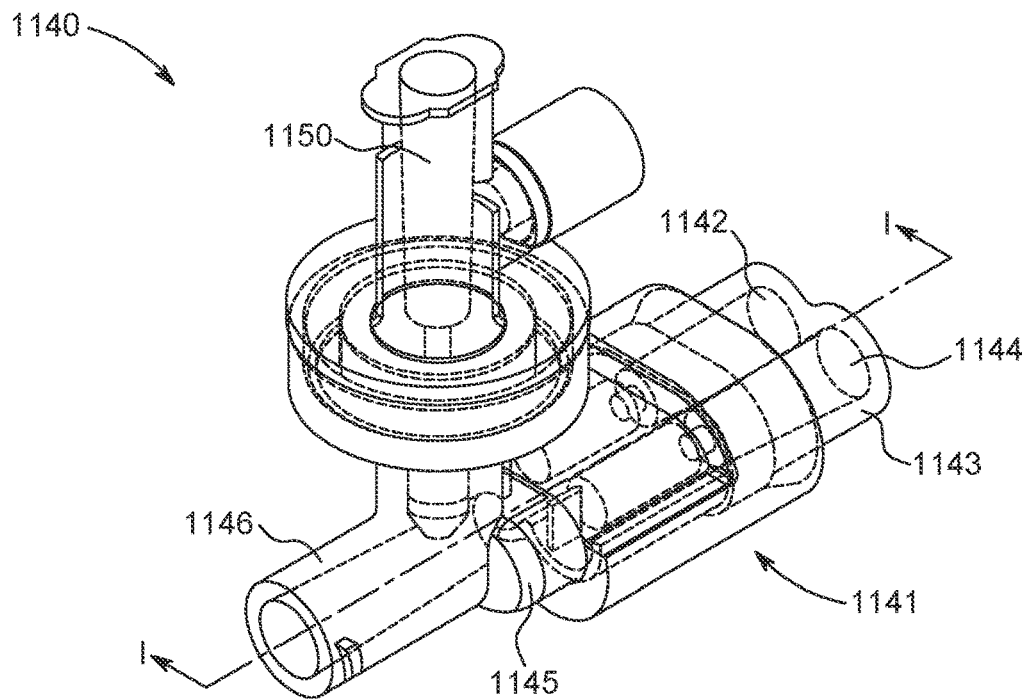
FIG. 28 is a perspective view of a fluid mixing device coupled with a pressure isolation valve according to another embodiment.
Figure 29:
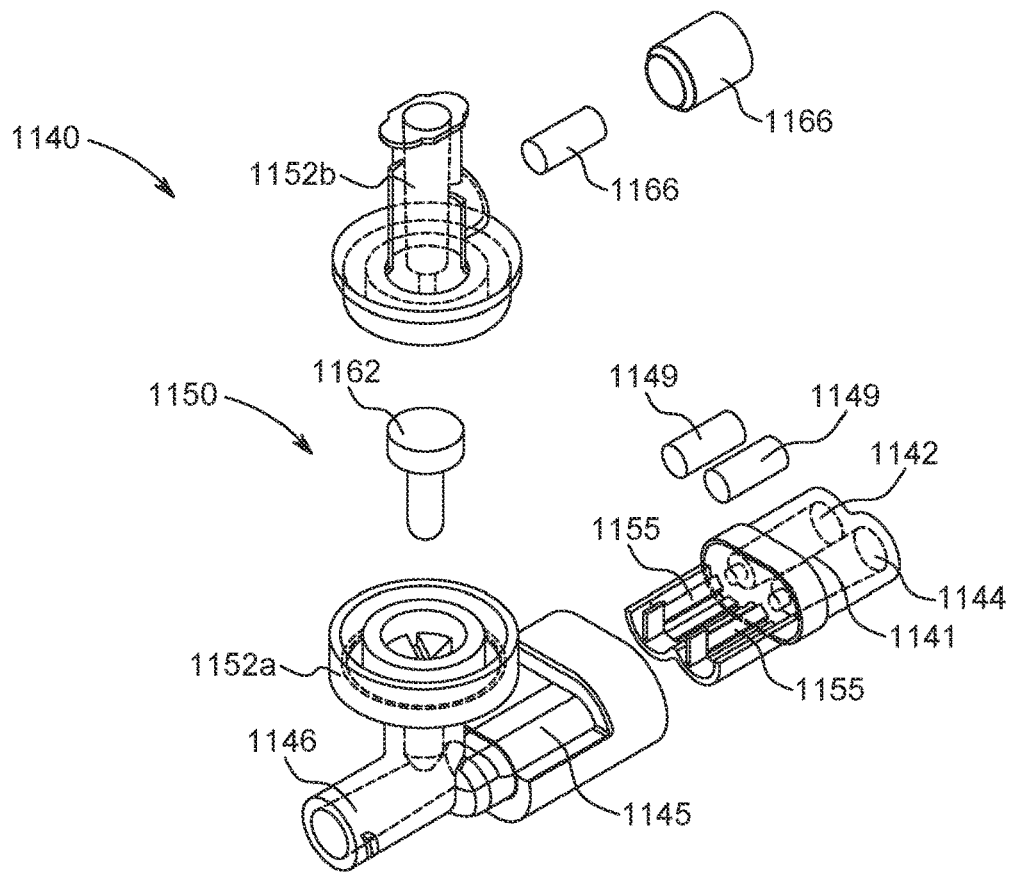
FIG. 29 is an exploded view of the fluid mixing device shown in FIG. 28.
Figure 30:
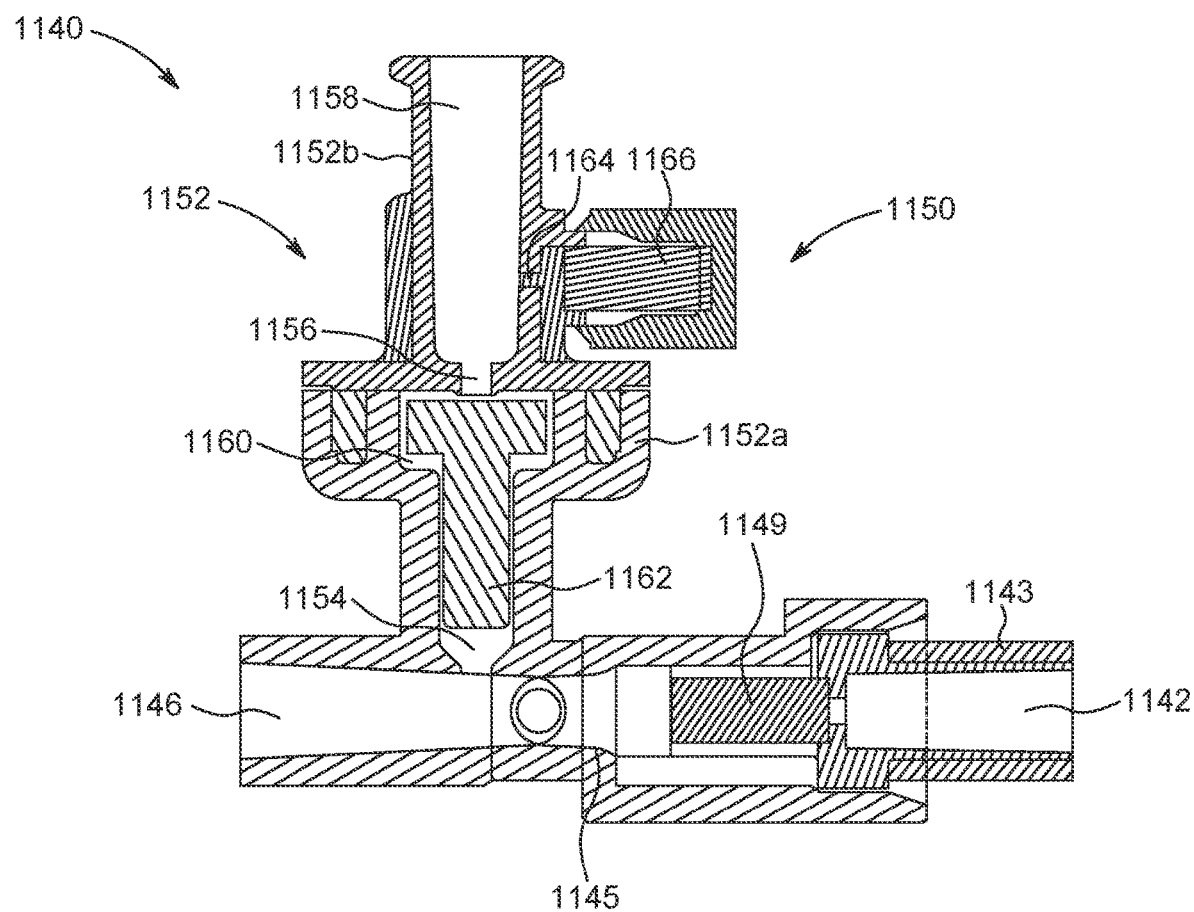
FIG. 30 is a cross-sectional view of the fluid mixing device of FIGS. 28-29, taken along line I-I in FIG. 28.

In another embodiment of the present disclosure, as shown in FIGS. 28-30, a fluid mixing device 1140 having a body 1141 defining first and second fluid inlets 1142 and 1144, each of which is configured to conduct a corresponding one of the first and second injection fluids. The body of the fluid mixing device 1140 further includes an outlet port 1146 configured for delivering a mixture of the first and second injection fluids to outlet tubing (not shown). The body 1141 with a first portion 1143 and a second portion 1145 that are non-removably or removably connected together. A check valve 1149 is disposed in a channel 1155 of each of the first and second fluid inlets 1142 and 1144 (shown in FIG. 29) and is configured to be opened under pressure to permit a flow of the first and second injection fluids toward the outlet port 1146. The structure and functionality of the fluid mixing device 1140 shown in FIGS. 28-30 is substantially identical to the structure and functionality of the fluid mixing device 1040 described herein with reference to FIGS. 22-27. Accordingly, only the relative differences between the two embodiments will now be discussed.

With reference to FIGS. 28-30, the outlet port 1146 may have a pressure isolation valve 1150 configured to allow for connecting a pressure transducer to the fluid path so that hemodynamic blood pressure signal readings may be obtained during fluid delivery. The pressure isolation valve 1150 isolates the high pressure fluid injector system from interfering with a low pressure measurement of a hemodynamic blood pressure signal.

The pressure isolation valve 1150 includes a housing 1152, which may be a unitary structure or, preferably, a multi-piece structure as shown in FIG. 29. For example, the housing 1152 is a two-piece housing including a first portion 1152a and a second portion 1152b, which are adapted to connect together to form the housing 1150. The first and second portions 1152a, 1152b are preferably formed for non-removable engagement with each other. Non-limiting examples of suitable pressure isolation valves are described in U.S. Pat. Nos. 6,866,654; 7,611,503; 8,919,384; and 8,992,489, the disclosures of which are incorporated by reference.

With reference to FIG. 30, the first portion 1152a of the housing 1152 defines a high pressure lumen 1154, which forms a high pressure side of the pressure isolation valve 1150. The high-pressure lumen 1154 is in fluid communication with the outlet port 1146. The second portion 1152b of the housing 1152 defines a low pressure lumen 1156, which generally forms a low pressure side of the pressure isolation valve 1150. The second portion 1152b of the housing 1152 further includes a pressure isolation port 1158 to which a pressure transducer (not shown) may be connected. The structure forming pressure isolation port 1158 may terminate in a luer connector or other suitable medical connector for connecting a pressure transducer to the pressure isolation port 1158.

The first and second portions 1152a, 1152b of the housing 1152 may define an internal chamber 1160 generally in fluid communication with the high pressure lumen 1154 and the low pressure lumen 1156. An internal valve member 1162 is located in the internal chamber 1160 and is biased to a normally open position, wherein the high pressure lumen 1154 is in fluid communication with the low pressure lumen 1156. The valve member 1162 is generally further adapted to isolate the low pressure lumen 1156 once fluid pressure in the high pressure lumen 1154 reaches a preset pressure. The low pressure lumen 1156 further includes a flow initiating port 1164 having a flow initiating valve 1166 that is generally adapted to initiate a small flow around the valve member 1162 such that the valve member 1162 operates to a closed position substantially upon flow initiation.

While various embodiments of fluid mixing devices for mixing two injection fluids have been described herein, similar fluid mixing devices with three or even four total fluid inlets, each having corresponding redirecting surfaces, where the fluid inlets are in fluid communication with a mixing chamber similar to as described herein. Such fluid mixing devices fall within the scope of the present disclosure.

While various embodiments of fluid mixing devices and patient fluid delivery tube sets were provided in the foregoing description, those skilled in the art may make modifications and alterations to these examples without departing from the scope and spirit of the disclosure. Accordingly, the foregoing description is intended to be illustrative rather than restrictive. The disclosure described hereinabove is defined by the appended claims, and all changes to the disclosure that fall within the meaning and the range of equivalency of the claims are to be embraced within their scope.

We claim:

1. A fluid delivery tube set for delivering fluid from a fluid injector to a patient, the fluid delivery tube set comprising:
   a first inlet tube configured to deliver a first injection fluid;
   a second inlet tube configured to deliver a second injection fluid;
   an outlet tube configured to deliver a mixture of the first injection fluid and the second injection fluid to the patient; and
   a fluid mixing device comprising:
      a first fluid inlet coupled to the first inlet tube and configured to conduct the first injection fluid in a first direction, the first fluid inlet having a first redirecting surface;
      a second fluid inlet coupled to the second inlet tube and configured to conduct the second injection fluid in a second direction, the second fluid inlet having a second redirecting surface;
      a mixing chamber in fluid communication with the first fluid inlet and the second fluid inlet and having a third redirecting surface, the mixing chamber configured to mix the first injection fluid and the second injection fluid, wherein the mixing chamber comprises a first inlet distal to the third redirecting surface and a second inlet distal to the third redirecting surface, wherein the first redirecting surface is positioned distal to the first fluid inlet and at least partially faces the first inlet to the mixing chamber, and wherein the second redirecting surface is positioned distal to the second fluid inlet and at least partially faces the second inlet to the mixing chamber; and an outlet port coupled to the outlet tube and in fluid communication with the mixing chamber, wherein the first redirecting surface is configured to redirect the first injection fluid in a first different direction from the first direction to enter the mixing chamber along the first different direction, and wherein the second redirecting surface is configured to redirect the second injection fluid in a second different direction from the second direction to enter the mixing chamber along the second different direction, wherein the first different direction and the second different direction are selected so that the first injection fluid and the second injection fluid contact the third redirecting surface of the mixing chamber to turbulently mix the first injection fluid and the second injection fluid together in the mixing chamber, and wherein the mixture of the first injection fluid and the second injection fluid exits the fluid mixing device via the outlet port.

2. The fluid delivery tube set of claim 1, further comprising at least one of a first check valve in the first fluid inlet; and a second check valve in the second fluid inlet.

3. The fluid delivery tube set of claim 2, wherein the first fluid inlet and the second fluid inlet have a non-circular cross-sectional shape, and wherein the first check valve and the second check valve have a circular cross-sectional shape.

4. The fluid delivery tube set of claim 2, wherein the first check valve has a first end in engagement with a first inlet port on the first fluid inlet and a second end in engagement with 35a first stop element proximal to the first redirecting surface, wherein the second check valve has a first end in engagement with a second inlet port on the second fluid inlet and a second end in engagement with a second stop element proximal to the second redirecting surface, and wherein the first check valve and the second check valve are reversibly compressible between the first end and the second end in response to a first fluid pressure of the first injection fluid flowing through the first inlet port and a second fluid pressure of the second injection fluid flowing through the second fluid port, respectively.

5. The fluid delivery tube set of claim 4, wherein the first stop element and the second stop element have a pointed proximal end.

6. The fluid delivery tube set of claim 4, wherein the first inlet port and the second inlet port have a tapered end surface.

7. The fluid delivery tube set of claim 1, wherein the first fluid inlet and the second fluid inlet have a first inlet port and a second inlet port, respectively, wherein the first redirecting surface and second redirecting surface are positioned distally relative to the first inlet port and second inlet port, respectively, and wherein the third redirecting surface is positioned proximally relative to the outlet port, the first redirecting surface, and the second redirecting surface.

8. The fluid delivery tube set of claim 1, wherein at least one of the first redirecting surface and the second redirecting surface has a substantially concave-shaped surface and has a radius of curvature greater than or equal to 90°.

9. The fluid delivery tube set of claim 1, wherein at least one of the first redirecting surface and the second redirecting surface has a substantially concave-shaped surface and has a radius of curvature greater than or equal to 150°.

10. The fluid delivery tube set of claim 1, wherein the third redirecting surface has a substantially concave-shaped surface facing the outlet port.

11. The fluid delivery tube set of claim 10, wherein the concave-shaped surface has a radius of curvature of greater than or equal to 90°.

12. The fluid delivery tube set of claim 10, wherein the concave-shaped surface has a radius of curvature of greater than or equal to 150°.

13. The fluid delivery tube set of claim 1, wherein the outlet port has an axis parallel to an axis of the first fluid inlet and an axis of the second fluid inlet.

14. The fluid delivery tube set of claim 13, wherein the axis of the outlet port extends between the axis of the first fluid inlet and the axis of the second fluid inlet.

15. The fluid delivery tube set of claim 1, wherein each of the first redirecting surface and the second redirecting surface are concave-shaped and face a direction of fluid flow of the first injection fluid in the first fluid inlet and a direction of fluid flow of the second injection fluid in the second fluid inlet, respectively.

16. The fluid delivery tube set of claim 1, wherein at least one of the first fluid inlet, the second fluid inlet, and the outlet port has an at least partially helical-shaped rifling on at least a portion of an inner surface of the at least one of the first fluid inlet, the second fluid inlet, and the outlet port for creating a corresponding fluid vortex for at least one of the first injection fluid, the second injection fluid, and the mixture of the first injection fluid and the second injection fluid, respectively.

17. The fluid delivery tube set of claim 1, wherein the outlet port has at least one baffle member or mixing member disposed in an inner surface thereof.

18. The fluid delivery tube set of claim 1, wherein the outlet port further comprises a pressure isolation valve integrated therewith.

19. The fluid delivery tube set of claim 18, wherein the pressure isolation valve comprises a housing having a first lumen in fluid communication with the outlet port, a second lumen configured for connecting to a pressure transducer, and a valve member between the first lumen and the second lumen, wherein the valve member is configured for isolating the second lumen from the outlet port during a fluid injection procedure.

20. The fluid delivery tube set of claim 1, further comprising a connector element on an exterior or an interior of at least one of a proximal end of the first fluid inlet, a proximal end of the second fluid inlet, and a distal end of the outlet port for connecting to a distal end of the first inlet tube, a distal end of the second inlet tube, and a proximal end of the outlet tube, respectively.

* * * * *

UNITED STATES PATENT AND TRADEMARK OFFICE
CERTIFICATE OF CORRECTION

| | | |
|---|---|---|
| PATENT NO. | : 12,070,568 B2 | Page 1 of 1 |
| APPLICATION NO. | : 18/324674 | |
| DATED | : August 27, 2024 | |
| INVENTOR(S) | : Cowan et al. | |

It is certified that error appears in the above-identified patent and that said Letters Patent is hereby corrected as shown below:

In the Specification

In Column 1, Line 8, delete "2022" and insert -- 2022, now U.S. Pat. No. 11,712,552, --, therefor.
In Column 15, Line 31, delete "the a" and insert -- a --, therefor.
In Column 15, Line 35, delete "do" and insert -- due --, therefor.
In Column 15, Line 36, delete "configured of" and insert -- configured for --, therefor.
In Column 17, Line 36, delete "the than the" and insert -- the --, therefor.

In the Claims

In Column 27, Line 38, in Claim 4, delete "35a" and insert -- a --, therefor.

Signed and Sealed this
Fourth Day of February, 2025

Coke Morgan Stewart
*Acting Director of the United States Patent and Trademark Office*